(12) United States Patent
Taki et al.

(10) Patent No.: US 8,784,317 B2
(45) Date of Patent: Jul. 22, 2014

(54) SIGNAL PROCESSING APPARATUS, ULTRASONIC APPARATUS, CONTROL METHOD FOR SIGNAL PROCESSING APPARATUS, AND CONTROL METHOD FOR ULTRASONIC APPARATUS

(75) Inventors: Hirofumi Taki, Kyoto (JP); Kenichi Nagae, Yokohama (JP); Toru Sato, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 185 days.

(21) Appl. No.: 12/995,536

(22) PCT Filed: Jul. 24, 2009

(86) PCT No.: PCT/JP2009/063623
§ 371 (c)(1),
(2), (4) Date: Dec. 1, 2010

(87) PCT Pub. No.: WO2010/013792
PCT Pub. Date: Feb. 4, 2010

(65) Prior Publication Data
US 2011/0083511 A1    Apr. 14, 2011

(30) Foreign Application Priority Data

Jul. 31, 2008 (JP) ................... 2008-198500
Mar. 5, 2009 (JP) ................... 2009-051886

(51) Int. Cl.
*A61B 8/00* (2006.01)

(52) U.S. Cl.
USPC ............ 600/442; 600/437; 600/443; 382/128

(58) Field of Classification Search
USPC ........... 600/407–429, 437–469; 382/128–132
See application file for complete search history.

(56) References Cited

U.S. PATENT DOCUMENTS

| 5,309,914 A | 5/1994 | Iinuma ........................ 600/443 |
| 5,469,850 A | 11/1995 | Iizuka et al. .................. 600/443 |

(Continued)

FOREIGN PATENT DOCUMENTS

| JP | 04-317641 | 11/1992 |
| JP | 2003-339696 | 12/2003 |

(Continued)

OTHER PUBLICATIONS

Office Action issued Apr. 24, 2012 in counterpart Chinese patent application 200980129082.7, with translation.

(Continued)

*Primary Examiner* — Sanjay Cattungal
(74) *Attorney, Agent, or Firm* — Fitzpatrick, Cella, Harper & Scinto

(57) ABSTRACT

A signal processing apparatus scans a beam of elastic waves into an object to be examined, acquires received waveform data of a plurality of scan lines, and performs signal processing to form a tomographic image of said object to be examined from the received waveform data of the plurality of scan lines. The signal processing apparatus includes a scan line correlation calculation part (009) that calculates a correlation value of received waveform data between a first scan line and a second scan line that has a prescribed correlation with the first scan line, for a plurality of positions on the scan lines, and a correlation change position extraction part (010) that extracts, from among the plurality of positions on said scan lines, a position at which the correlation value becomes a value different from a prescribed value as a position at which a unique region can exist.

30 Claims, 18 Drawing Sheets

(56) References Cited

U.S. PATENT DOCUMENTS

| | | | |
|---|---|---|---|
| 6,689,061 B2 * | 2/2004 | Hayasaka | 600/437 |
| 2002/0183619 A1 * | 12/2002 | Hayasaka | 600/443 |
| 2006/0079780 A1 | 4/2006 | Karasawa | 600/447 |
| 2007/0167802 A1 * | 7/2007 | Rigby et al. | 600/459 |
| 2008/0306371 A1 | 12/2008 | Fukutani et al. | 600/407 |
| 2009/0275837 A1 | 11/2009 | Shiina et al. | 600/459 |
| 2009/0299185 A1 | 12/2009 | Oikawa et al. | 600/447 |
| 2011/0204893 A1 * | 8/2011 | Sumi | 324/318 |

FOREIGN PATENT DOCUMENTS

| | | |
|---|---|---|
| JP | 2005-169155 | 6/2006 |
| WO | WO 02/095444 | 11/2002 |

OTHER PUBLICATIONS

Office Action issued on Oct. 28, 2013 in counterpart PRC patent application 200980129082.7, with translation.

* cited by examiner

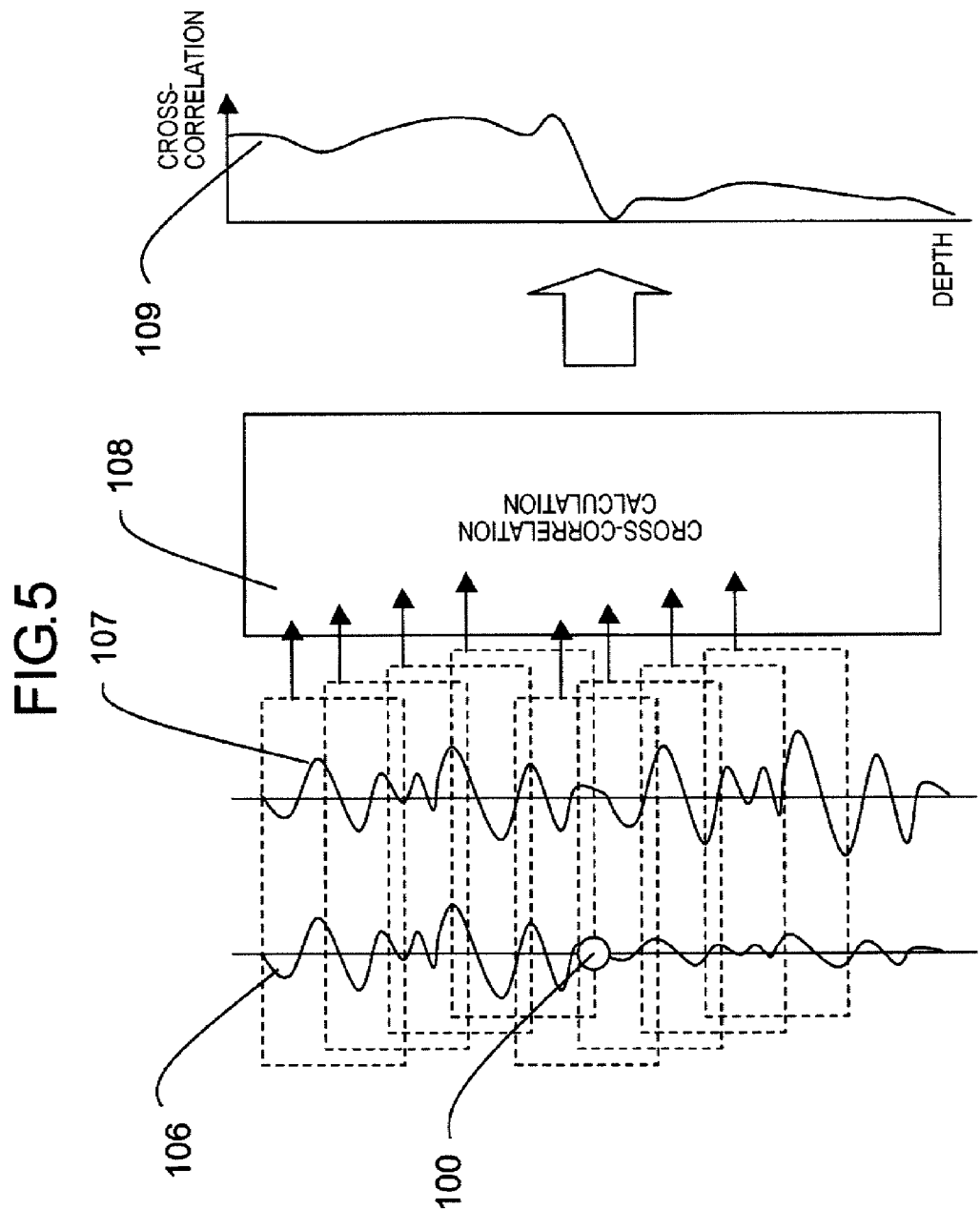

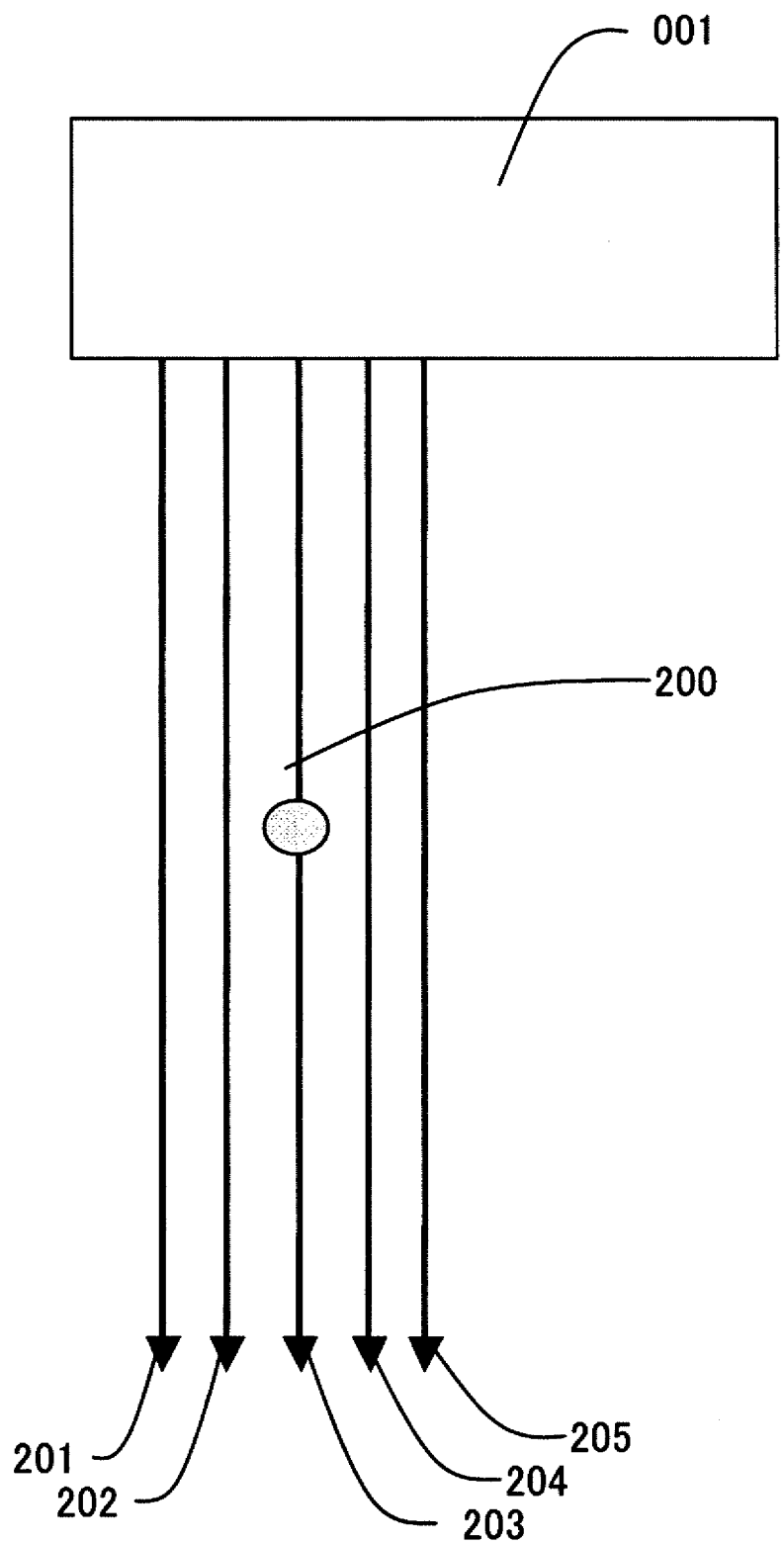

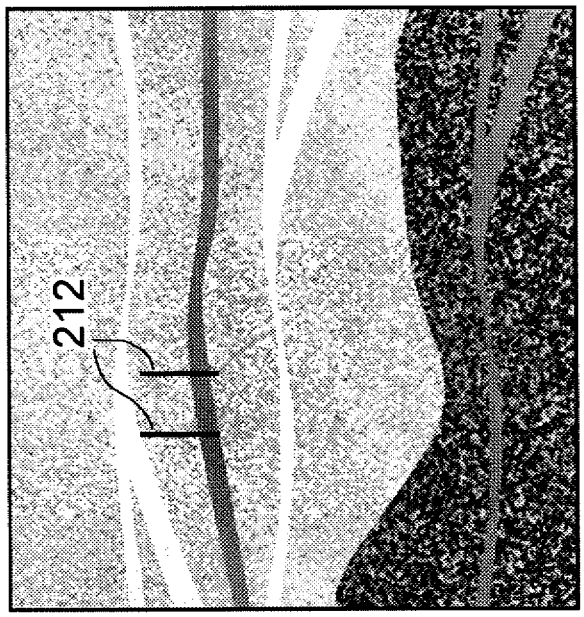
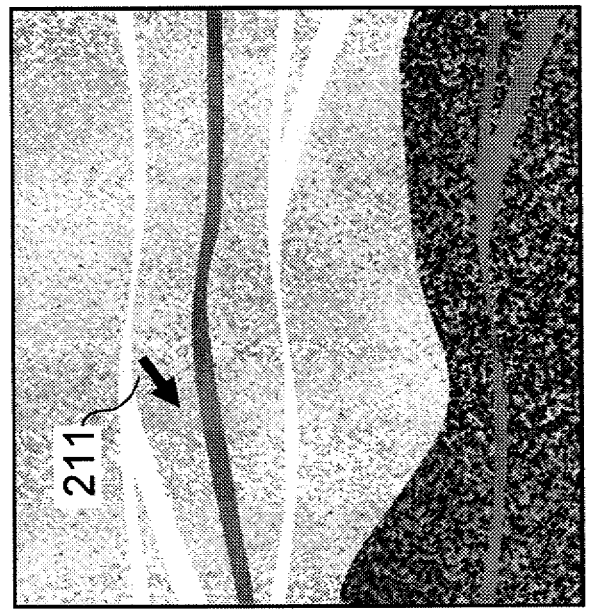

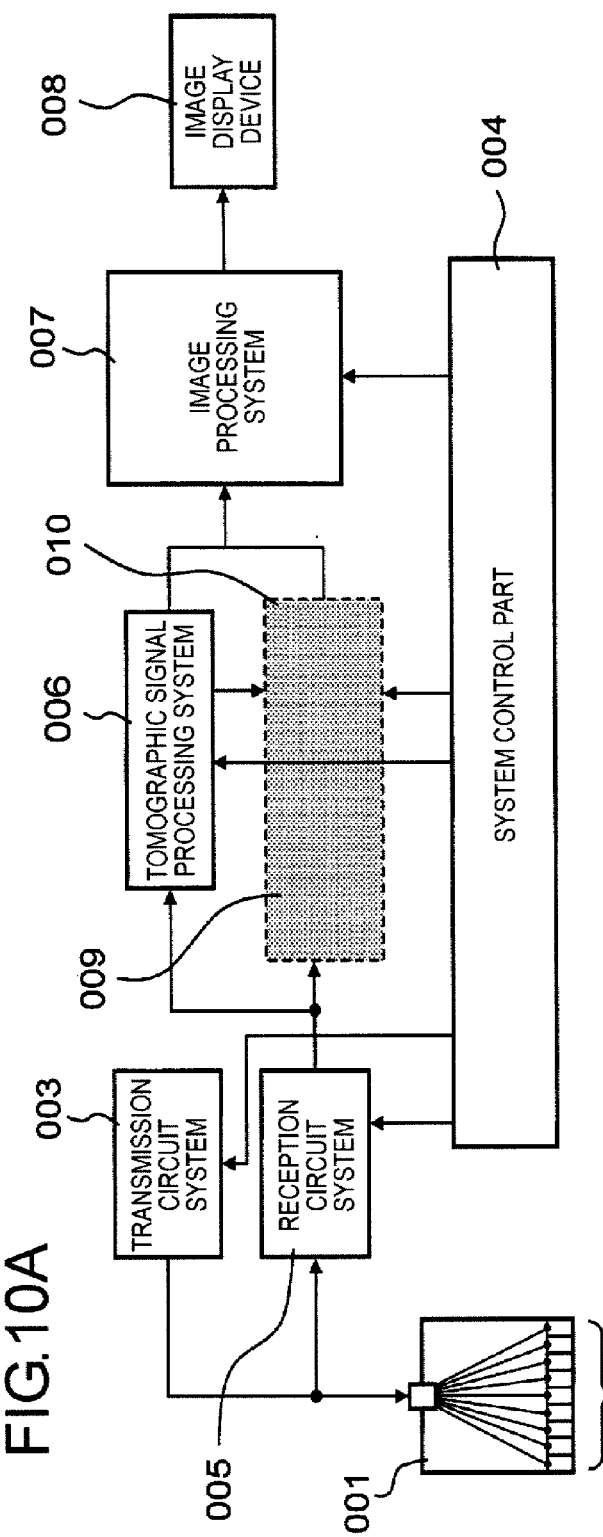
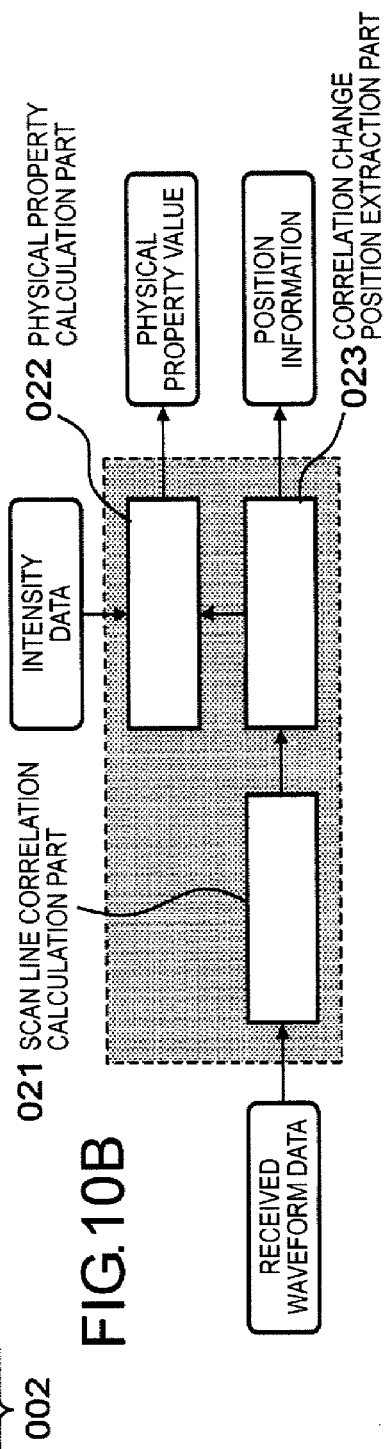
FIG.10A
FIG.10B

… (1)

SIGNAL PROCESSING APPARATUS, ULTRASONIC APPARATUS, CONTROL METHOD FOR SIGNAL PROCESSING APPARATUS, AND CONTROL METHOD FOR ULTRASONIC APPARATUS

TECHNICAL FIELD

The present invention relates to a signal processing apparatus and an ultrasonic apparatus that acquire a tomographic image or a three-dimensional image of a sample by using ultrasonic waves in the form of elastic waves, and in particular, it relates to a signal processing apparatus and an ultrasonic apparatus for detecting a unique region such as a reflector of high reflectivity, etc.

Also, the present invention relates to a control method for a signal processing apparatus and a control method for an ultrasonic apparatus for acquiring a tomographic image or a three-dimensional image of a sample by using ultrasonic waves in the form of elastic waves, and in particular, it relates to a control method for a signal processing apparatus or a control method for an ultrasonic apparatus for detecting a unique region such as a reflector of high reflectivity, etc.

BACKGROUND ART

A conventional apparatus for obtaining a tomographic image by using ultrasonic waves in the form of general elastic waves has a transmission part for transmitting ultrasonic waves in the form of elastic waves to a sample, a reception part for receiving reflected waves, and a scanning unit for scanning the transmission and reception waves. Further, provision is made for a unit for converting and visualizing a received reflected signal into a luminance signal. Thus, the interior of the sample is observed by using the time series tomographic images obtained by the above-mentioned units. In addition, in one form of the above-mentioned apparatus, a three-dimensional image is obtained by scanning an ultrasonic wave in the up and down directions as well as in the right and left directions by means of the above-mentioned scanning unit.

Now, a living body is taken as one of objects to be observed by ultrasonic waves. Ultrasonic waves have real time, handiness, non-invasiveness, and so on, which become advantages, and hence ultrasonic waves are often used to observe the interior of a living body.

Ultrasonic waves used to observe the interior of a living body are transmitted and received by a plurality of electromechanical transducers (mainly piezoelectric elements).

At the time of transmission, ultrasonic waves converging into a focal position are generated by providing electric signals to a plurality of elements in a time shifted manner so that the phases of the ultrasonic waves coincide with each other at the focal position. A region through which the ultrasonic waves generated by such driving pass is a region around a straight line connecting between the center of the plurality of elements thus driven and the focal position, and this may be sometimes called a transmission beam. Upon reception of reflected waves, the reflected signals of the ultrasonic waves at the focal position are acquired by correcting their time delays corresponding to the focal position so as to add them to the electric signals, respectively, which have been generated from the received ultrasonic waves by means of the plurality of elements. The reflected signals thus added by the electric signals from the plurality of elements become received waveform data holding the waveforms of the ultrasonic waves. Then, the received waveform data is converted into intensity data by acquiring an envelope of this received waveform data (also referred to as envelope detection). An image is finally formed by thinning or rounding this intensity data according to the pixels of the image to be displayed, and further interpolating the thus thinned or rounded intensity data as required. Here, note that the focal position at the time of the reception can be caused to change in real time. In addition, a region of the focal position generated by the reception processing of the aforementioned transmission beam may be called a received beam.

By performing such transmission and reception control, it becomes possible for the ultrasonic apparatus to image the interior of the living body by transmitting ultrasonic waves to a part to be observed, and receiving waves reflected therefrom. Here, note that a linear region acquired by these transmission beam and received beam is called a scan line, and an image is formed by arranging a plurality of pieces of data each for such a scan line in parallel to one another.

Since ultrasonic waves are able to image the interior of a living body in a non-invasive manner according to the above-mentioned principles, they are widely used for detecting various forms of the interior of the living body. Among such various forms, there is the detection of a high reflector such as a calculus. One of detection methods for a calculus which have been frequently carried out in the field of medical care is a technique that detects a calculus depending on whether an acoustic shadow is generated in an image at a rear side of the calculus, i.e., at a side far from a search unit or probe or at a deeper region. Here, note that the acoustic shadow is a shadow portion in which an image behind a high reflector is not formed because ultrasonic pulses do not reach behind the high reflector and receiving beams are interrupted by the high reflector.

In Japanese patent application laid-open No. 2003-339696, there is disclosed an ultrasonic apparatus that acquires the correlation of adjacent scan lines so as to set the density of the scan lines, and controls, as a result thereof, a transmission beam former or a reception beam former. Also, in Japanese patent application laid-open No. 2005-169155, there is disclosed an ultrasonic apparatus that extracts the outline of a tissue based on image data.

In addition, in Japanese patent application laid-open No. H04-317641, there is disclosed an ultrasonic imaging apparatus that detects a linear boundary in a tomographic image or a boundary surface in three-dimensional information by the use of the phase information of reflected waves. As a specific means, there is disclosed one that calculates, from a designated position, times at which the cross-correlation functions of the individual scan lines become maximized, and positions obtained from those times are connected to one another so that outline or contour information in a sample to be examined and a continuous boundary of an object are displayed.

SUMMARY OF THE INVENTION

However, the above-mentioned acoustic shadow can not sometimes be generated easily depending on the position, the size, and the shape of the high reflector, and in that case, the extraction of the high reflector becomes difficult. One such case is when a technique of moving a focal position at the time of reception of a reflected beam in real time, as described above, is adopted. In this technique, it is possible to thin the received beams at all the depths to be observed, and, therefore, has an advantageous effect that the resolution of an entire image can be improved. Now, description will be given while referring to FIG. 1. In FIG. 1, 100 denotes a high reflector, 101 a reception focus, and 102 a received beam. For instance, in case where the reception focus 101 is set to a position that is deeper than the high reflector 100, the width of the received beam 102 expands at a depth where the high reflector exists, as a result of which the ultrasonic waves passing through the sides of the high reflector are received. Therefore, it becomes difficult to generate an acoustic shadow due to the high reflector 100, and a search for the acoustic shadow becomes difficult. In addition, the intensity of a reflected wave (also called a reflected echo or a reflected signal) of a beam focused to the high reflector can sometimes be small depending on the size or the shape of the high reflector. For instance, in case where the size of the high reflector is small (e.g., when the diameter of the reflector is 1 mm or less under the assumption that the shape of the high reflector is approximated by a spherical ball), the intensity of the reflected wave detected by a detector becomes small. In addition, in case where the shape is non-uniform (e.g., in case of including, in part, a flat surface or irregularities, or in case of being of asymmetrical shape, etc.) with a reflection surface of the highest reflectance not existing on a detector side, the intensity of the reflected wave detected by the detector becomes small. That is, even with a high reflector, a small detection signal may result. In such a case, the difference in signal intensity between a reflected wave obtained at the position of the high reflector and those obtained in its surroundings becomes small.

Further, as stated above, final image data can be obtained by processing the individual ultrasonic signals received by the elements, respectively, in the following manner. That is, image data is acquired by obtaining (1) received waveform data according to time delay correction and addition processing and (2) intensity data through the acquisition of an envelope thereof, and by performing (3) thinning, rounding and interpolation processing on the intensity data thus obtained. However, a lot of information may be lost from the ultrasonic signals in such processes. For example, in case where a reflected echo intensity from the high reflector and a reflected echo intensity from a planar tissue interface are substantially the same level, the reflected echo from the high reflector may be buried in the reflected echo from the tissue interface on an image. FIG. 2A through FIG. 3B are views diagrammatically showing such a situation. FIG. 2A illustrates that the high reflector 104 is arranged in a simulated tissue 103. The transmission and reception of ultrasonic waves are performed with an ultrasonic probe 001 being arranged on an upper surface of the simulated tissue 103. FIG. 2B is a graph in which the intensities of echoes reflected from depths of A-A', B-B' and C-C', respectively, in FIG. 2A are diagrammatically plotted. In the graph of FIG. 2B, the high reflector is arranged in the vicinity of the center of the horizontal axis. As can be seen from the graph, echoes from the high reflector protrude above reflected echoes from its surrounding tissues. Next, FIG. 3A illustrates the simulated tissue 103 in which a lamellar tissue or structure 105 is arranged without a high reflector. The lamellar tissue 105 has a reflectance which is set lower than that of the high reflector. FIG. 3B is a graph in which the intensities of reflected echoes from depths of A-A', B-B' and C-C', respectively, in FIG. 3A are diagrammatically plotted. In the graph of FIG. 3B, a solid line denoted by a legend "high reflector A-A'" is plotted with the intensities of reflected echoes from the high reflector of FIG. 2B being superimposed thereon. As can be seen from this graph, even the intensities of reflected echoes from the lamellar structure of low reflectance are about the same as the intensities of reflected echoes from the high reflector of high reflectance. Thus, it is difficult to determine based solely on the intensities of reflected echoes whether a high reflector exists. That is, a signal having a certain degree of intensity can be detected even in the case of the absence of a high reflector.

Further, in case where a speckle pattern is generated by the interference of reflected echoes from a minute scatterer and the reflected echoes of a high reflector exist together therein, it is difficult to extract those signals which originate only in the minute scatterer in a selective manner, and to discriminate them from other signals. In particular, in case where the high reflector is small and appears as a point-like echo on an image, it becomes more difficult to discriminate the high reflector.

Here, note that the ultrasonic imaging apparatus described in Japanese patent application laid-open No. H04-317641 is an apparatus that calculates, from the designated position, positions with time shifts therefrom at which the cross-correlation functions between the individual scan lines become maximized, and displays a boundary by connecting these positions with one another. Accordingly, in case where a high reflector exists as a point-like echo (i.e., when any echo is not detected on adjacent scan lines), there will be no other positions to be connected with the point-like echo in its surrounding (i.e., the one point of the high reflector position only exists). Therefore, it is difficult to extract the high reflector by applying the technique described in Japanese patent application laid-open No. H04-317641.

In the cases as referred to above, in order to extract the information of the presence or absence and the position of a high reflector, there is required a technique with further high sensitivity which takes into consideration a feature(s) specific to the high reflector, rather than using image data.

The present invention has been made in view of the above-mentioned problems, and provides a technique which is capable of detecting the position of the possible existence of a unique region (peculiar region, specific region) such as a high reflector from received waveform data of elastic waves. In addition, the present invention provides a technique that assists to detect a unique region by means of ultrasonic diagnostics. Further, the present invention provides a technique that is capable of estimating the physical property values of a unique region.

The present invention in a first aspect provides a signal processing apparatus which scans a beam of elastic waves into an object to be examined, acquires received waveform data of a plurality of scan lines, and performs signal processing to form a tomographic image of the object to be examined from the received waveform data of the plurality of scan lines, the apparatus having: a scan line correlation calculation part that calculates a correlation value of received waveform data between a first scan line and a second scan line that has a prescribed correlation with the first scan line, for a plurality of positions on the scan lines; and a correlation change position extraction part that extracts, from among the plurality of positions on the scan lines, a position at which the correlation value becomes a value different from a prescribed value as a position at which a unique region can exist.

The present invention in a second aspect provides a signal processing apparatus which performs signal processing on signals obtained by receiving reflected signals of elastic waves from inside an object to be examined so as to form an image, the apparatus having: a scan line correlation calculation part that calculates and outputs, from received waveform data of at least two mutually close scan lines of the reflected signals, a correlation value between the close scan lines; and a discrimination part that extracts position information in a depth direction inside the object to be examined from a change in the correlation value, and discriminates the kind of a unique region inside the object to be examined based on the correlation value after the change.

The present invention in a third aspect provides an ultrasonic apparatus which scans a beam of ultrasonic waves, which are elastic waves, into an object to be examined, acquires received waveform data of a plurality of scan lines, and performs signal processing to form a tomographic image of the object to be examined from the received waveform data of the plurality of scan lines, the apparatus having: a scan line correlation calculation part that calculates a correlation value of received waveform data between a first scan line and a second scan line that has a prescribed correlation with the first scan line, for a plurality of positions on the scan lines; and a correlation change position extraction part that extracts, from among the plurality of positions on the scan lines, a position at which the correlation value becomes a value different from a prescribed value as a position at which a high reflector can exist.

The present invention in a fourth aspect provides a control method for a signal processing apparatus which acquires received waveform data of a plurality of scan lines reflected inside an object to be examined, and performs signal processing to form a tomographic image of the object to be examined from the received waveform data of the plurality of scan lines, the method including: a scan line correlation calculation step that calculates a correlation value of received waveform data between a first scan line and a second scan line that has a prescribed correlation with the first scan line, for a plurality of positions on the scan lines; and a correlation change position extraction step that extracts, from among the plurality of positions on the scan lines, a position at which the correlation value becomes a value different from a prescribed value as a position at which a unique region can exist.

The present invention in a fifth aspect provides a control method for an ultrasonic apparatus which acquires received waveform data of a plurality of scan lines reflected inside an object to be examined, and forms a tomographic image of the object to be examined from the received waveform data of the plurality of scan lines, the method including: a scan line correlation calculation step that calculates a correlation value of received waveform data between a first scan line and a second scan line that has a prescribed correlation with the first scan line, for a plurality of positions on the scan lines; and a correlation change position extraction step that extracts, from among the plurality of positions on the scan lines, a position at which the correlation value becomes a value different from a prescribed value as a candidate for a position at which a high reflector can exist.

The present invention in a sixth aspect provides a signal processing apparatus which scans a beam of elastic waves into an object to be examined, acquires received waveform data of a plurality of scan lines, and performs signal processing to form a tomographic image of the object to be examined from the received waveform data of the plurality of scan lines, the apparatus having: a scan line correlation calculation part that calculates a correlation value of received waveform data between a first scan line and a second scan line that has a prescribed correlation with the first scan line, for a plurality of positions on the scan lines; and a processing part that applies, to a distribution in a scanning direction of a cross-correlation value calculated for a predetermined depth, transformation processing that transforms a first distribution shape with drops at opposite ends of a unique region of a predetermined size into a second distribution shape with a drop in a central position of the unique region, and estimates a position at which the unique region can exist by using the result of the transformation processing.

The present invention in a seventh aspect provides a signal processing apparatus which scans a beam of elastic waves into an object to be examined, acquires received waveform data of a plurality of scan lines, and performs signal processing to form a tomographic image of the object to be examined from the received waveform data of the plurality of scan lines, the apparatus having: a scan line correlation calculation part that calculates correlation values of received waveform data between a first scan line and a second scan line that has a prescribed correlation with the first scan line, for a plurality of positions on the scan lines; a correlation change position extraction part that extracts, from among the plurality of positions on the scan lines, a position at which the correlation value becomes a value different from a prescribed value as a position candidate for a position at which a unique region can exist; and a processing part that applies, to a distribution in a scanning direction of a cross-correlation value calculated for a noted region set based on the position candidate, transformation processing that transforms a first distribution shape with drops at opposite ends of a unique region of a predetermined size into a second distribution shape with a drop in a central position of the unique region, and estimates a position at which the unique region can exist by using the result of the transformation processing.

The present invention in an eighth aspect provides a control method for a signal processing apparatus which scans a beam of elastic waves into an object to be examined, acquires received waveform data of a plurality of scan lines, and performs signal processing to form a tomographic image of the object to be examined from the received waveform data of the plurality of scan lines, the method including: a scan line correlation calculation step that calculates a correlation value of received waveform data between a first scan line and a second scan line that has a prescribed correlation with the first scan line, for a plurality of positions on the scan lines; a transformation processing step that applies, to a distribution in a scanning direction of a cross-correlation value calculated for a predetermined depth, transformation processing that transforms a first distribution shape with drops at opposite ends of a unique region of a predetermined size into a second distribution shape with a drop in a central position of the unique region; and an estimation step that estimates a position at which the unique region can exist by using the result of the processing in the transformation processing step.

According to the present invention, it is possible to detect the candidates of the positions of existence of a unique region such as a high reflector, etc., from the received waveform data of ultrasonic waves typically in the form of elastic waves, thus making it possible to assist the detection of the unique region by means of ultrasonic diagnostics. In addition, according to an ultrasonic apparatus of the present invention, it is possible to estimate the physical property values of the unique region. In particular, a minute high reflector can be detected with high precision.

Further features of the present invention will become apparent from the following description of exemplary embodiments with reference to the attached drawings.

BRIEF DESCRIPTION OF DRAWINGS

FIG. 5 is a view explaining a technique for calculating a cross-correlation.

FIG. 6 is a view for explaining adjacent scan lines.

FIG. 7A and FIG. 7B are displayed examples of the position information of a tomographic image and a high reflector, respectively.

FIG. 10A and FIG. 10B are block diagrams of an ultrasonic apparatus according to a third embodiment of the present invention.

DESCRIPTION OF EMBODIMENTS

Figure 1:
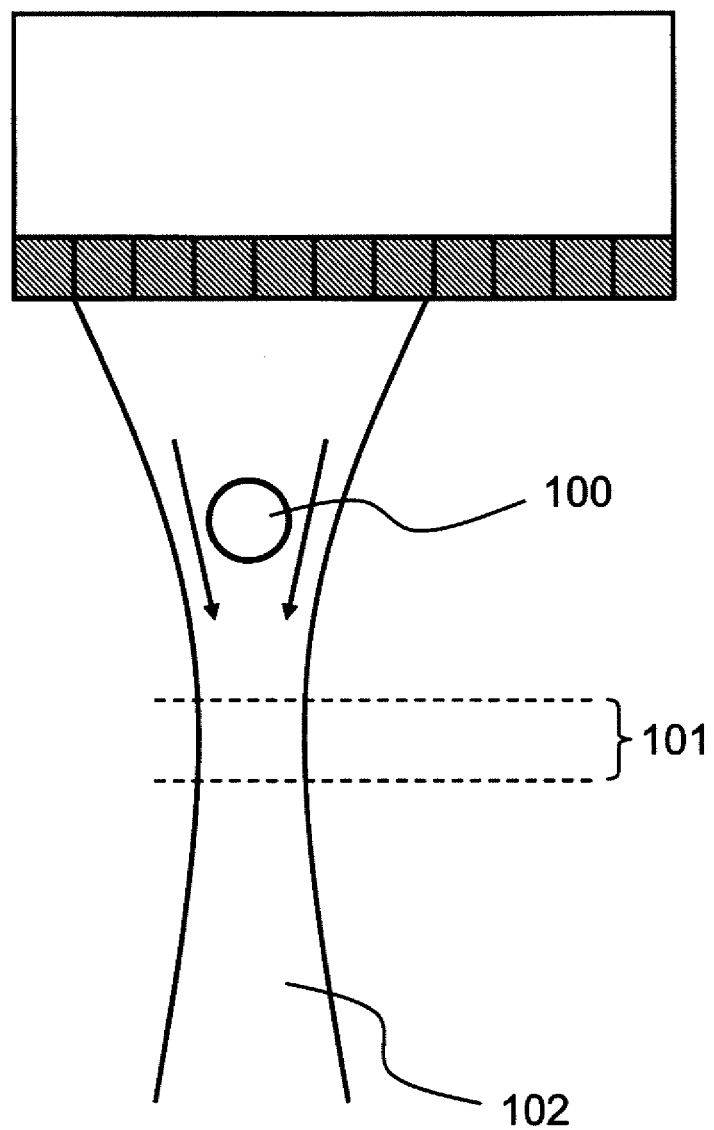
FIG. 1 is a view for explaining the extent of the width of a received beam.

In the present invention, elastic waves mean oscillating waves including ultrasonic waves.

In the present invention, a unique region (peculiar region, specific region) means a region that is in a state different from its surrounding inside an object or sample to be examined. For example, it means a region of which the composition, structure, physical properties and the like are different from those of its surrounding, and which is a region having a lamellar tissue or structure, or a region that is made a high reflector for ultrasonic waves typically due to calcification or the like.

The size of a high reflector that is one target to be detected in the present invention means a ball having a diameter of 2 mm or less under the assumption that the high reflector is approximated by the spherical shape of a ball. In addition, a diameter of 1 mm or less is preferable, and in particular, a diameter of 100 micrometers (μm) or less is more preferable. In case where the minute high reflector is approximated by the spherical shape of a ball, if the diameter of the ball becomes equal to or less than 2 mm, according to conventional methods, a reflected wave itself becomes so small that the detection thereof becomes difficult, or a signal of a reflected wave is lost in surrounding signals so the discrimination thereof becomes difficult.

In addition, in the present invention, the presence or absence of a high reflector is detected by extracting a position in which a correlation value (also referred to as a cross-correlation value) between scan lines decreases. Therefore, if the data of individual scan lines having a correlation value equal to or more than a certain fixed value in the absence of a high reflector is used, it is possible to detect a minute high reflector. According to inventors' findings, even with those individual scan lines which have a cross-correlation of about 0.5, for instance, the detection of a high reflector can be made.

In order to improve the accuracy of detection of a high reflector, it is desirable to use scan lines with a cross-correlation higher than that. For instance, two close scan lines or two adjacent scan lines can be the scan lines with a high cross-correlation.

In the present invention, the relation between a first scan line and a second scan line for which the above-mentioned cross-correlation is to be calculated means those which have a relation satisfying the following requirement. That is, the above-mentioned correlation value between the first scan line and the second scan line should be such that the correlation value between the first scan line and the second scan line is 0.5 or more in a region inside an object to be examined in which there exist no high reflectors. In addition, it is suitable in the present invention that the correlation value is preferably 0.7 or more, and most preferably 0.9 or more.

Here, further description will be given to the above-mentioned correlation value between the first scan line and the second scan line. When the correlation value between the first scan line and the second scan line is 1.0, it is meant that the first scan line and the second scan line are the same wave (signal). In addition, when the correlation value between the first scan line and the second scan line is 0, it is meant that the first scan line and the second scan line are waves (signals) that are greatly (typically completely) different from each other. Then, it is meant that the higher the correlation value between the scan lines, the more similar the states of distribution of the acoustic impedance in regions where reflected waves (reflected echoes, reflected signals) have been generated are to each other. When imaging is carried out by means of ultrasonic waves, if adjacent scan lines have an overlapped region within the range of a beam width, the correlation value between the adjacent scan lines has a constant or fixed value, and hence it is desirable to transmit beams at such an interval that an overlapped region can be obtained within the range of a beam width.

In the present invention, when one of the other scan lines is reflected by a high reflector with the above-mentioned correlation value being 0.5 or more, it is possible to obtain a significant difference between the above-mentioned correlation value (the correlation value before reflected by the high reflector) and a correlation value between the first scan line and the second scan line at a position that is deeper than the position of the high reflector.

In addition, the present invention can make a discrimination between a high reflector (in particular, a minute calcified portion, etc.) in the form of a reflector having a constant reflectance and a lamellar structure inside an object to be examined. (A large-sized high reflector can be discriminated even with the use of a conventional technique because the high reflector includes a high reflection region which is large in area.)

According to the present invention, a position in which a high reflector or a lamellar structure can exist is specified from a change of the correlation value between the close or adjacent scan lines, and the high reflector and the lamellar structure can be discriminated based on changes of the correlation value at positions that are shallower and deeper than that position. That is, in the case of a (minute) high reflector, only one of two scan lines that are close or adjacent to each other is reflected by the (minute) high reflector, whereas the other scan line is not reflected. In contrast to this, in the case of a lamellar structure, the lamellar structure is sufficiently larger than the minute high reflector, so both of two close or adjacent scan lines are reflected. Thus, in the case of the (minute) high reflector, the correlation value of two close or adjacent scan lines indicates a large value up to a position at which the high reflector exists, and at a position deeper than the position at which the (minute) high reflector exists, the above-mentioned correlation value become small. On the other hand, in the case of the lamellar structure, the correlation value of two close or adjacent scan lines indicates a large value up to a position at which the lamellar structure exists. In addition, even at positions that are deeper than the position at which the lamellar structure exists, the correlation value does not substantially change (an amount of change is limited).

Thus, according to the present invention, a high reflector can be discriminated, based on a reference position at which the high reflector or the lamellar structure exists, when the correlation value of two close or adjacent scan lines becomes smaller at a position which is deeper than the above-mentioned reference position, and a lamellar structure can be discriminated when there is no chance or a little change in the correlation value. In addition, a signal processing apparatus or ultrasonic apparatus of the present invention can be provided with a discrimination part that discriminates the high reflector and the lamellar structure from each other based on the above-mentioned discrimination method as required.

According to this inventors' findings, it is desirable that the above-mentioned first scan line and second scan line be mutually in a relation in which the correlation thereof is strong (large), and typically, two scan lines that are adjacent to each other are desirable. However, in case where the relation of the above-mentioned correlation values is satisfied, the first scan line and the second scan line are not necessarily required to be adjacent to each other, but another scan line (s) can exist between these scan lines. Accordingly, it is possible to make use of two scan lines that are close to each other within a range to satisfy the above-mentioned relation.

Figure 13:
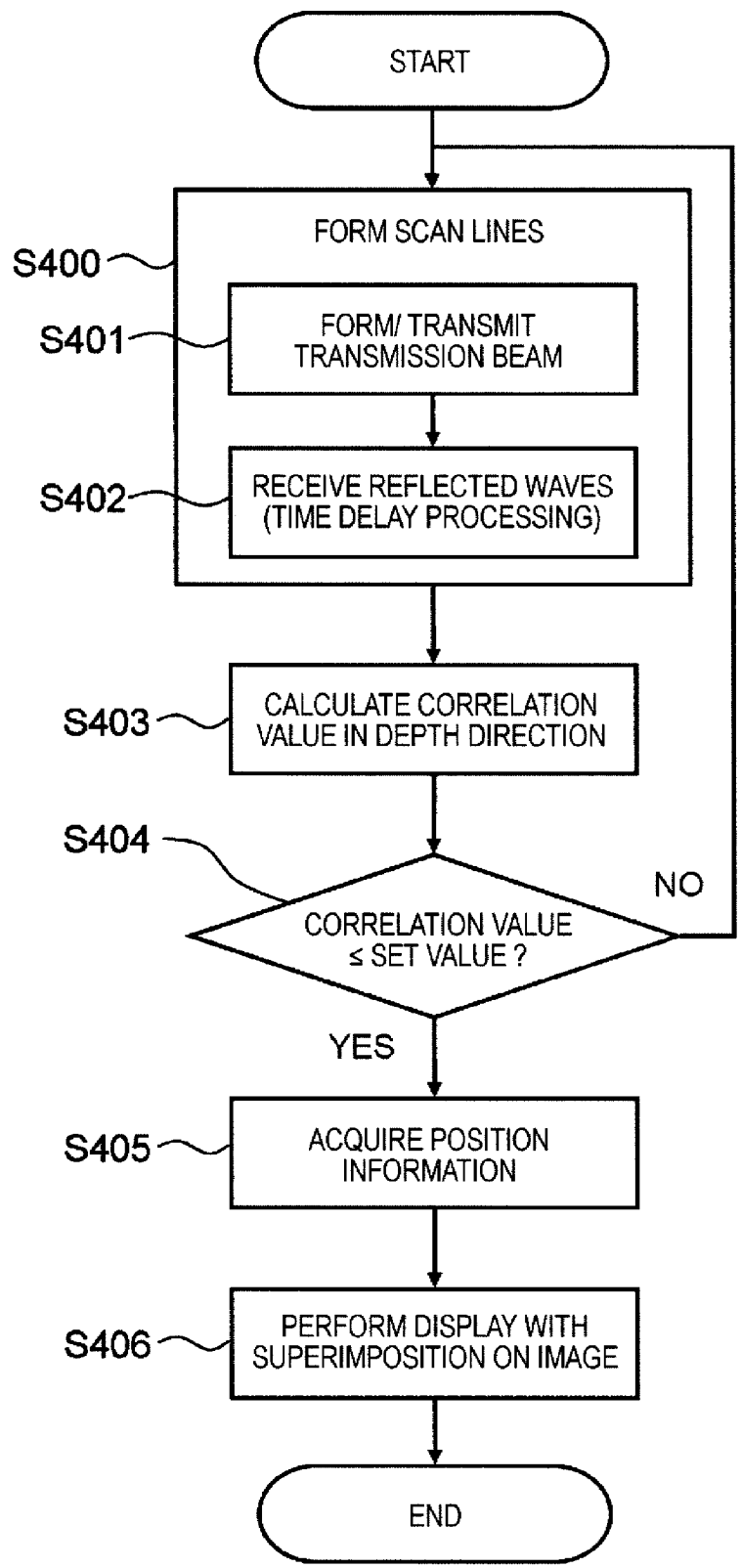
FIG. 13 is a flow chart explaining one procedure for obtaining a correlation value according to the present invention.

FIG. 13 illustrates a flow chart that describes one procedure for obtaining the correlation value of the present invention. First of all, as a premise to form scan lines (S400), it is required that the correlation value between the first scan line and the second scan line in a region including no high reflector be 0.5 or more. Then, transmission beams satisfying the above-mentioned requirement are formed and transmitted to an object to be examined (S401). A reflected wave from a specific position inside the object to be examined is received (S402), and a correlation value thereof in a depth direction inside the object to be examined is calculated and compared with a set value which has been set beforehand (S404). When the result of the comparison satisfies a predetermined condition, position information is acquired (S405). When the comparison result does not satisfy the predetermined condition, a return is made to (S400), where a reflection wave reflected at a position different from and deeper in a depth direction than the position at which the previous reflection wave was reflected and received is received again. Such a series of steps are repeated until all the positions in the depth direction of the object to be examined are inspected, or until the comparison result satisfies the predetermined condition. After position information is acquired in a step of S405, the information is superimposed on an image (S406). The above-mentioned procedure is one example, and the present invention is not limited to the above-mentioned procedure.

Figure 15:
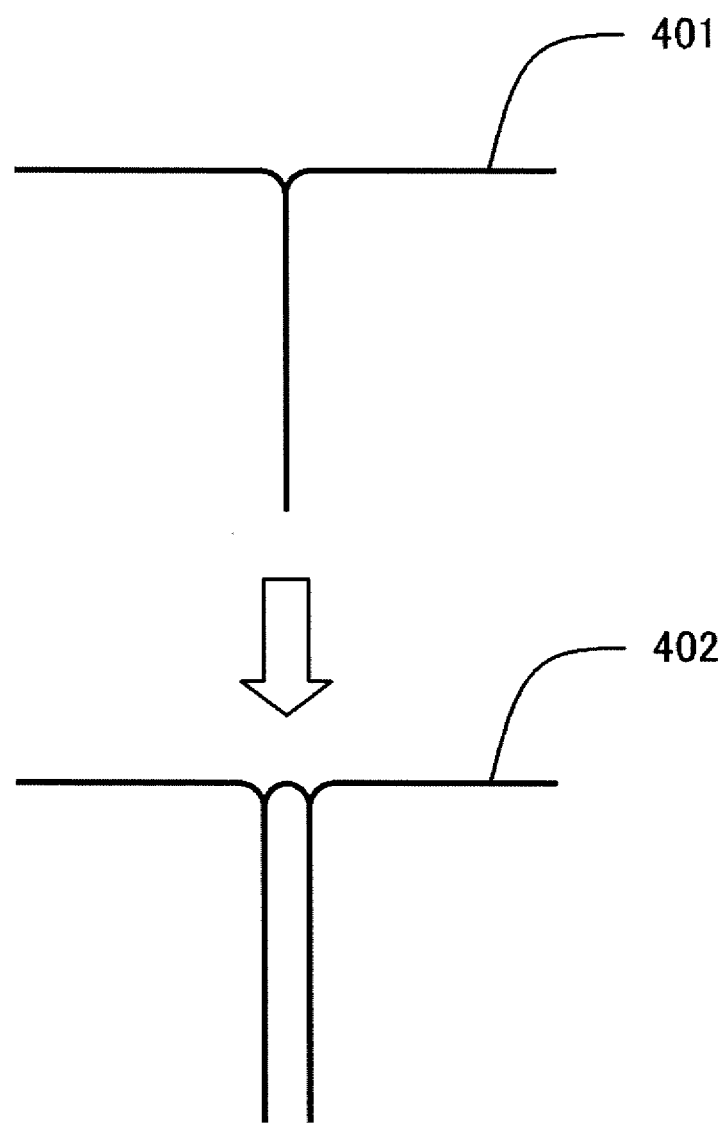
FIG. 15 is a view modeling the relation between the position of the high reflector and the cross-correlation according to the fifth embodiment of the present invention.

Next, reference will be made to correlation filtering processing in the present invention by using FIG. 15. When looking at a distribution in a scanning direction (i.e., a direction substantially perpendicular to a scan line) of cross-correlation values calculated for a predetermined depth (a certain noted depth at which information is to be acquired), even with a single high reflector, drops or decreases in the correlation values may be generated at a plurality of locations in a depth in which the high reflector exists or in a position that is deeper than that depth. FIG. 15 depicts a model in which the correlation value decreases at opposite ends of a high reflector. A numeral 401 in FIG. 15 denotes a function f with a drop in the position of the existence of the high reflector. It can be said that this function f shows an ideal cross-correlation value distribution under the assumption that the size of the high reflector is small enough. In case where the cross-correlation value distribution shows a profile like the function f, the position of the high reflector in the form of a unique region can be specified with high precision. However, in actuality, the high reflector has a finite size and reflects a plurality of scan lines, so a profile like the function f is not obtained, and a drop or decrease in the correlation value appears in two places at the opposite ends of the high reflector, as shown like a cross-correlation value distribution g denoted by a numeral 402.

Here, when considering that an ideal function f is observed while being transformed into the cross-correlation value distribution g, and representing such a transformation matrix by H, their relation can be expressed by the following equation.

$$g=Hf$$

Here, note that the transformation matrix H is a matrix that changes in accordance with the beam width and the size of the high reflector. The transformation matrix H can be calculated by giving a filtering parameter corresponding to an estimated size of the high reflector. In addition, by using a filtering parameter corresponding to a different size, it is possible to calculate a transformation matrix H corresponding to each reflector size. Here, it is preferable that the estimated size of the high reflector be 2 mm or less, but it is also possible to set a parameter corresponding to a size of 2 mm or more.

From the above-mentioned relation, it is understood that the ideal function f can be estimated from the cross-correlation value distribution g calculated for the certain noted depth and the given transformation matrix H. This estimation processing corresponds to the correlation filtering processing of the present invention. That is, the correlation filtering processing is the processing that estimates the function f with a drop at the position of the high reflector from the cross-correlation value distribution g calculated for a certain noted depth. In other words, the correlation filtering processing is the processing that applies transformation processing, which transforms a first function (a first distribution shape) with drops at opposite ends of a high reflector of a predetermined size into a second function (a second distribution shape) with a drop in a central position of the high reflector, to a distribution g in a scanning direction of a cross-correlation value calculated for a certain noted depth. Also, it can be said that the correlation filtering processing is the processing that applies an inverse transformation of the processing, which transforms a second function (a second distribution shape) with a drop in a central position of a high reflector into a first function (a first distribution shape) with drops at opposite ends of the high reflector, to the above-mentioned cross-correlation value distribution g. Thus, the existence position of the high reflector can be clarified by applying the correlation filtering processing to the cross-correlation value distribution g calculated from a plurality of scan lines.

Since the transformation matrix H varies according to the size of the high reflector, the correlation filtering processing is the processing that depends on the size of the high reflector. In case where the size of the high reflector is already known, correlation filtering processing corresponding to the size need only be done. However, in case where the size of the high reflector is unknown, it is preferable to perform a plurality of correlation filtering processings by changing the estimated size of the high reflector (i.e., changing the filtering parameter). In this case, all the results of the plurality of filtering processings may be displayed, or after comparison of these results, only the best result may be adopted and displayed. Here, not that it is also possible to estimate the size of the high reflector from these comparison results.

In the above-mentioned correlation filtering processing, filter processings according to a variety of kinds of inverse filter design techniques including a Wiener filter are applicable. In addition, it is also possible to use a simple pattern matching technique.

Hereinafter, preferred embodiments of the present invention will be described in detail by way of example while referring to the accompanying drawings. Also, reference will be made to apparatuses and methods using supersonic waves as elastic waves.

First Embodiment

Hereinafter, in a first embodiment, description will be given to a supersonic apparatus that calculates a cross-correlation of adjacent scan lines and indicates position information in which the correlation becomes equal to or less than a set value.

Figure 4:
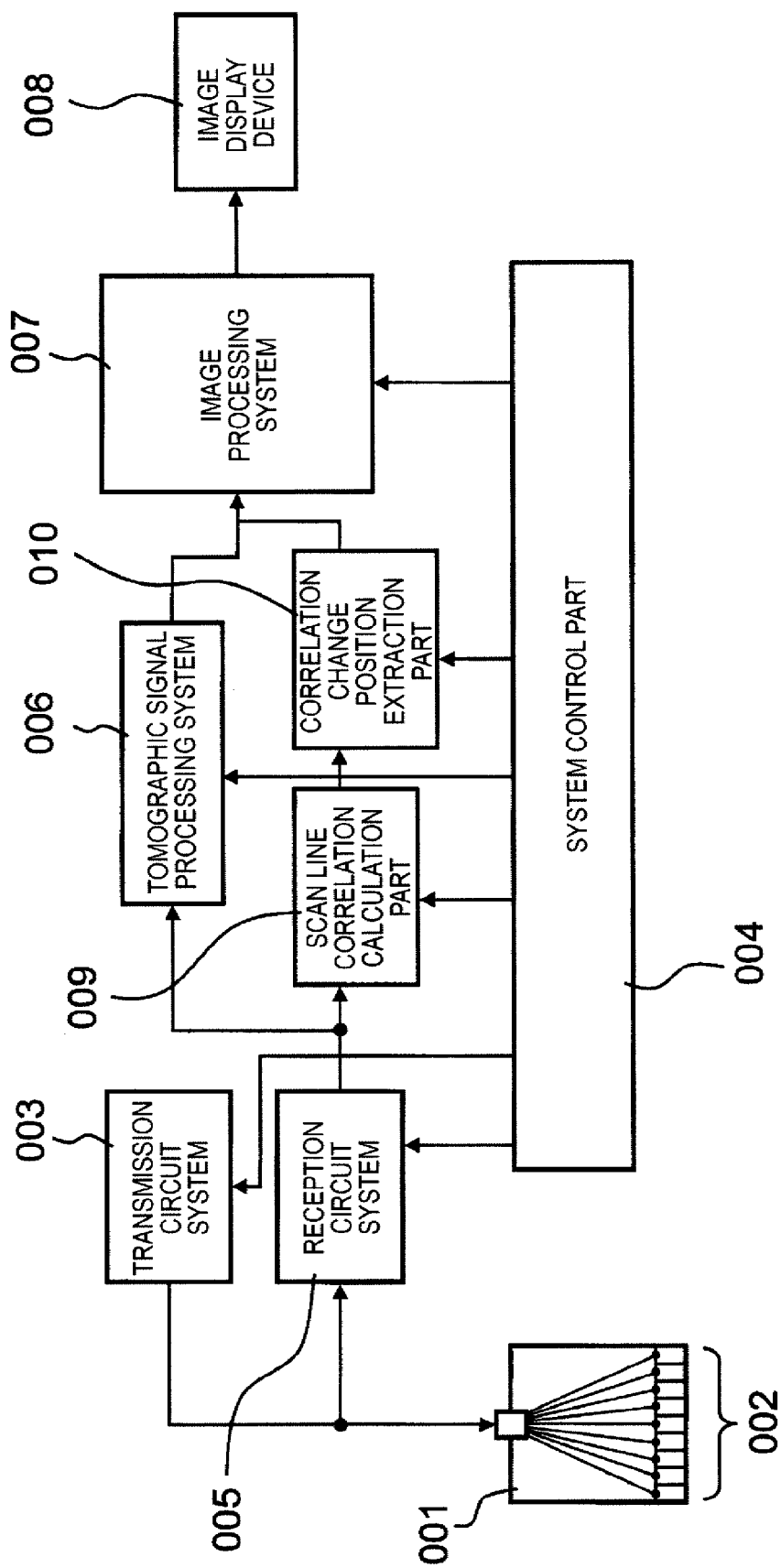
FIG. 4 is a block diagram of an ultrasonic apparatus according to a first embodiment of the present invention.

FIG. 4 is a system schematic diagram showing the ultrasonic apparatus according to the first embodiment of the present invention. This ultrasonic apparatus has a function to generate and display an ordinary ultrasonic tomographic image, and a function to detect a high reflector in a living body and to display candidates for the existence position thereof (a scan line correlation calculation part 009 and a correlation change position extraction part 010). For instance, the latter function is used for the detection of a calculus, a minute calcification region, etc.

(Generation and Display of Tomographic Image)

First of all, a flow until a tomographic image is displayed will be described by using FIG. 4. The ultrasonic apparatus of this embodiment is a system to which an ultrasonic probe 001 having a plurality of transducers 002 is connected. When a position for transmitting ultrasonic waves (a transmission focus) is set, the setting information is sent from a system control part 004 to a transmission circuit system 003. The transmission circuit system 003 transmits an electric signal to drive the plurality of transducers 002 in the ultrasonic probe 001 after deciding time delays and signal intensities based on the information. This electric signal is converted into displacements in the transducers 002, respectively, and is propagated as ultrasonic waves through the interior of an object to be examined. The ultrasonic waves thus propagated form a linear sound pressure distribution in the interior of the object to be examined. This is called a transmission beam. The ultrasonic waves propagated in the object to be examined return to the transducers 002 as echoes scattered and reflected due to acoustic characteristics inside the object to be examined. These echoes are converted into electric signals by means of the transducers 002, and these electric signals are input to a reception circuit system 005. In the reception circuit system 005, after amounts of time delays are calculated based on the information on the position of the reception focus given from the system control part 004, and time delay processing is performed on the input time series electric signals, which are then added to one another. According to this processing, reflected waves (also called reflected echoes) at the position of the reception focus inside the object to be examined can be selectively extracted. A region having reception sensitivities thus formed by such processing is called a reception or received beam in contrast to the transmission beam.

The time series received waveform data thus obtained is sent from the reception circuit system 005 to a tomographic signal processing system 006. In the tomographic signal processing system 006, an envelope of the input time series received waveform data, after being subjected to filtering processing such as band-pass filtering as necessary, is detected and output as intensity data. This intensity data is transmitted to an image processing system (image processing part) 007. The image processing system 007 generates a luminance signal at each position in a region to be observed by thinning, rounding or interpolating the data according to the pixels of an image to be displayed by using the transmission beam sent from the system control part 004 and the position information and the intensity data of the received beam. An image for one scan line is formed by such a series of operations. The directions and the positions of the transmission beam and the received beam are changed, and another scan line is formed in a different region inside the object to be examined by performing similar processing again while changing the directions or positions of the transmission beam and the reception beam. Tomographic images of the region to be observed can be formed by forming a plurality of scan lines in the region to be observed in this manner. The image processing system 007 transmits the tomographic images thus obtained to the image display device 008 and displays them thereon.

Here, note that a scan line formed by one transmission beam and one received beam has been described as one example. However, the present invention is not limited to this, but is also applicable to a technique for concurrently forming a plurality of scan lines by forming a plurality of reception beams for one transmission. In addition, the present invention is not limited to a two-dimensional tomographic image, but is also applicable when a three-dimensional region is observed.

(Detection and Display of High Reflector)

Next, reference will be made to the processing of detecting a high reflector(s) and a candidate(s) of the existence position (s) thereof by using FIG. 4 through FIG. 6.

As shown in FIG. 4, the ultrasonic apparatus is provided with the scan line correlation calculation part 009 and the correlation change position extraction part 010. The time series received waveform data generated by the reception circuit system 005 is sent to the scan line correlation calculation part 009. The scan line correlation calculation part 009 calculates cross-correlations along a time base between adjacent scan lines from the received waveform data and information of scan line positions sent from the system control part 004. FIG. 5 illustrates a conceptual diagram thereof. The received waveform data 106 of a first scan line is denoted by $S_1(r)$, and the received waveform data 107 of an adjacent second scan line is denoted by $S_2(r)$. The scan line correlation calculation part 009 sets a noted position (noted depth) on each scan line, extracts waveform data in a region of a predetermined width based on the noted position from each received waveform data, and performs a calculation 108 of cross-correlations between the extracted waveform data. A correlation value (also called a cross-correlation value) of the noted position is obtained by this calculation operation. Then, the correlation values of a plurality of positions (depths) on the scan lines can be calculated by repeating the above-mentioned calculation operation while moving the noted position in the depth direction (in the time base direction of the received waveform data). The change in the depth direction of the correlation values calculated in this manner is illustrated in a graph 109 of FIG. 5. For instance, a correlation value is calculated as a maximum value for the τ of Y(τ) in equation 1.

$$Y(\tau) = \frac{\left|\int_{R-\Delta r}^{R+\Delta r} S_1(r) \cdot S_2(r+\tau) dr\right|}{\sqrt{\int_{R-\Delta r}^{R+\Delta r} S_1^2(r) dr \cdot \int_{R-\Delta r}^{R+\Delta r} S_2^2(r+\tau) dr}} \quad (1)$$

Here, note that R denotes a noted depth (noted position), and Δr denotes a width in which the cross-correlation thereof is acquired. The cross-correlations in the depth direction are calculated by changing the noted depth R. Δr is set to be in a range of from about the wave length of a transmitting ultrasonic wave to several tens of times of the wave length.

In addition, the cross-correlations can be calculated according to equation 2 by denoting analytic signals obtained by applying a Hilbert transform to the received waveform data by $T_1(r), T_2(r)$.

$$\frac{\int_{R-\Delta r}^{R+\Delta r} |T_1(r) \cdot T_2(r)| dr}{\int_{R-\Delta r}^{R+\Delta r} |T_1(r)| dr \cdot \int_{R-\Delta r}^{R+\Delta r} |T_2(r)| dr} \quad (2)$$

FIG. 5 illustrates an example in which a high reflector 100 exists on a first scan line. It is understood that the cross-correlation 109 decreases at positions deeper than that of the high reflector 100.

Now, reference will be made to adjacent scan lines by using FIG. 6. FIG. 6 is a view that diagrammatically illustrates the ultrasonic probe 001, five scan lines 201, 202, 203, 204, 205 formed inside the object to be examined, and a high reflector 200. For instance, in case where the data of the scan line 202 is acquired after the acquisition of the data of the scan line 201, these scan lines 201, 202 are mutually adjacent to each other, so the scan line correlation calculation part 009 calculates a cross-correlation between the scan lines 201, 202. For instance, in case where the order of acquisition of the scan lines is an order of scan line 201, scan line 203, scan line 205, scan line 202, and scan line 204, the data of adjacent scan lines is acquired when the scan line 202 is first acquired. Accordingly, at that time, the scan line correlation calculation part 009 calculates a cross-correlation value between the scan lines 201, 202.

The scan line correlation calculation part 009 calculates the cross-correlation of the received waveform data of two scan lines along the time base (along the depth of the object to be examined). Since the adjacent scan lines are set in such a manner that parts of their regions to be observed mutually overlap with each other, it is general that they indicate a high correlation. For instance, a cross-correlation between the scan line 204 and the scan line 205 has a value equal to or more than a fixed value until a certain deep position in the object to be examined. However, focusing on the scan line 202 and the scan line 203, the high reflector 200 exists on the scan line 203. Therefore, the cross-correlation between the scan line 202 and the scan line 203 has values equal to or larger than a certain fixed value in a portion shallower than the high reflector 200, similar to the cross-correlation of the scan lines 204, 205, but decreases therefrom in a portion deeper than the high reflector 200. The correlation values along the depth having such a property are transmitted from the scan line correlation calculation part 009 to the correlation change position extraction part 010.

As stated above, when the high reflector exists in the object to be examined, there appears a decrease in the correlation value in the position (depth) of the high reflector. Typically, the correlation value changes from a first value into a second value in the position (depth) of the high reflector. Accordingly, the correlation change position extraction part 010 of this embodiment extracts a position in which the correlation value decreases by a value equal to or more than a prescribed value (greatly) from a predetermined condition. Then, the extracted position is output as a candidate for the existence position of the high reflector.

In addition, it is considered that even in case where a plurality of high reflectors exist in depth direction of one scan line in a discrete manner, an amount of change of the correlation value at each of the positions (depths) of the respective high reflectors is large as compared with the case where no high reflector exists, so the correlation values at the positions (depths) of the respective high reflectors can be candidates for the existence positions of the high reflectors.

A determination as to whether a correlation value is different from (typically, significantly lower than) the prescribed value (including the predetermined condition) can be made, for example, according to whether the rate of change (the rate of decrease) of the correlation value along the depth direction is larger than a predetermined value. Alternatively, by comparing the correlation value with a prescribed set value (threshold), a position at which the correlation value becomes smaller than the set value can be regarded as a position at which the correlation value decreases greatly from the predetermined condition. In this embodiment, the latter determination technique is adopted. In the following, a detailed description thereof will be given.

The correlation change position extraction part 010 takes, as its input values, the position information of the scan line and the set value (threshold) transmitted from the system control part 004, and the cross-correlations along the depth of the scan line transmitted from the scanning line correlation calculation part 009 (a scan line correlation calculation step). Then, a position at which the correlation value becomes equal to or less than the set value is extracted (a correlation change position extraction step), and is transmitted to the image processing system 007. At least a horizontal position (position in the scanning direction) and a depth are included in the position information transmitted to the image processing system 007.

The image processing system 007 superimposes the position information thus input on a tomographic image, and transmits it to the image display device 008. FIG. 7A and FIG. 7B are displayed examples of the position information obtained from the correlation change position extraction part, wherein the positions at which a decrease in the cross-correlation is detected are denoted by markers such as an arrow 201, a segment 202, etc. Here, note that besides these, any expression can be employed which is capable of informing the detected positions to an operator, such as changing the hue of the tomographic image, circling the detected positions, or the like.

Figure 2A:
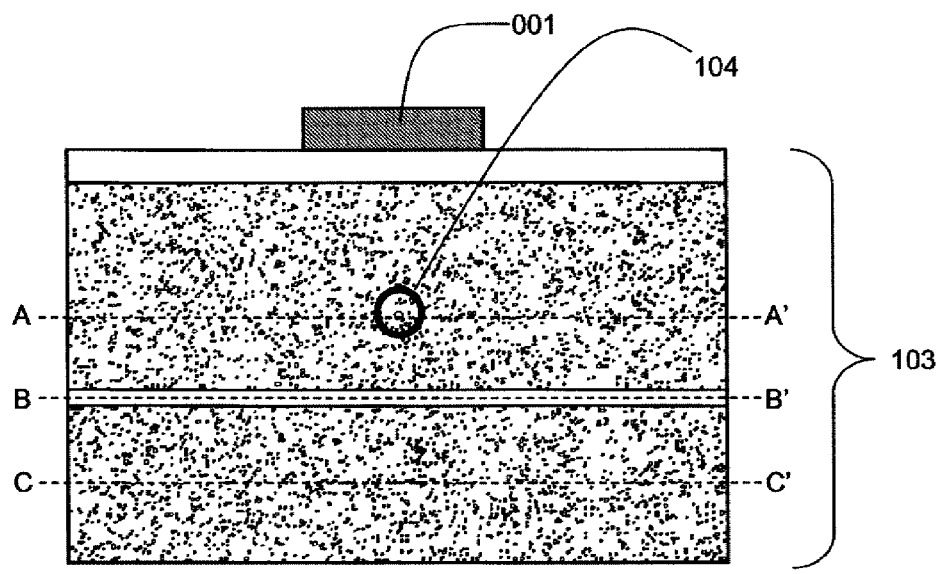
FIG. 2A is a view of a pseudo tissue model in which a high reflector exists.
Figure 2B:
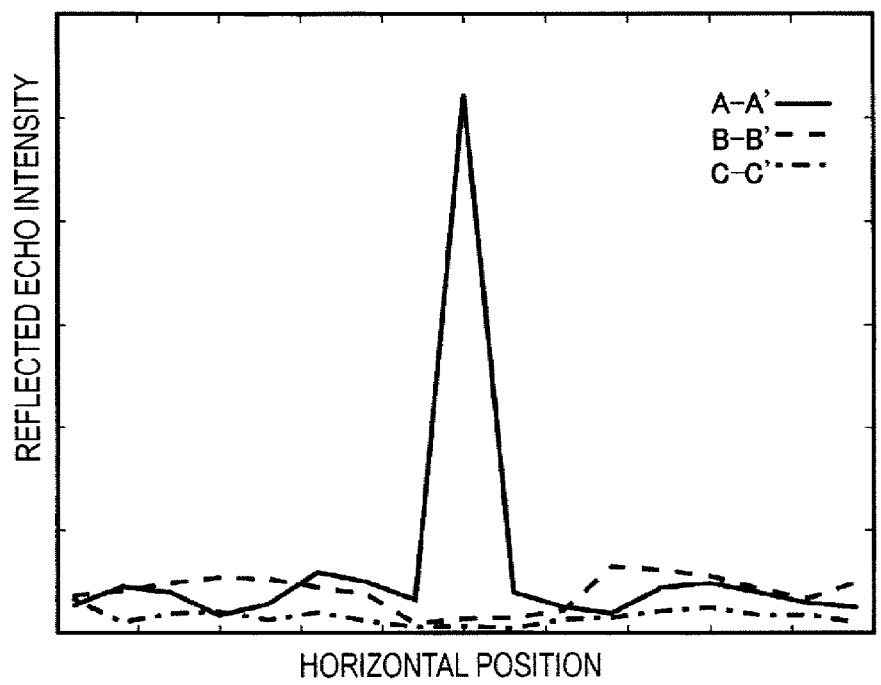
FIG. 2B is a view showing the intensities of reflected echoes therefrom.
Figure 8A:
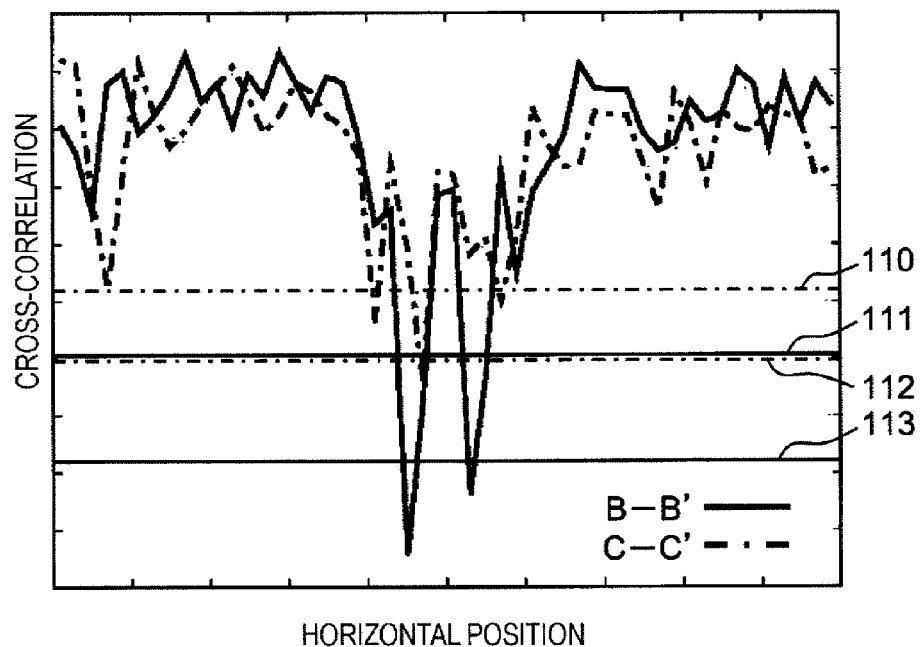
FIG. 8A and FIG. 8B are graphs in which cross-correlations thereof are plotted.

In the following, reference will be made to the effects of this embodiment by using FIG. 2A, FIG. 8A and FIG. 8B. As stated above, FIG. 2A illustrates that the high reflector 104 is arranged in the simulated tissue 103. FIG. 8A is a graph in which the values of the cross-correlations between adjacent scan lines in the vicinity of cross sections B-B' and C-C' in FIG. 2A are plotted. The axis of abscissa represents horizontal positions (the scanning direction), and the axis of ordinate represents the values of cross-correlations. The high reflector 104 is arranged in the vicinity of the center of the axis of abscissa. Both of the cross sections B-B' and C-C' are at positions that are deeper than that of the high reflector 104, so it is understood that the cross-correlation between adjacent scan lines decreases at a position at which the high reflector exists, i.e., in the vicinity of the center of the axis of abscissa.

Thus, in the case of existence of the high reflector 104, the cross-correlation between adjacent scan lines decreases significantly in portions that are deeper than the high reflector. Therefore, it is possible to show a candidate for the position at which the high reflector 104 exists by extracting a position at which the cross-correlation between adjacent scan lines decreases. Even if the intensity of a reflected echo itself resulting from the high reflector is small, it becomes possible to show the position candidate in which the high reflector 104 exists by performing control/processing as stated above based on the relation of the cross-correlation between adjacent scan lines.

Here, note that an initial value of the set value (threshold) for extracting the position in which the cross-correlation decreases is a value that is obtained by subtracting X times a standard deviation from the value of the cross-correlation at the same depth, e.g., an average value of cross-correlations on the cross section B-B'. Then, a position having a cross-correlation that is lower than this value is made a position candidate in which the high reflector exists. A set value 110 in FIG. 8A is a value for the data on the cross section C-C' in the case of X=2, and a set value 111 is a value for the data on the cross section B-B' in the case of X=2. In addition, a set value 112 is a value for the data of the cross section C-C' in the case of X=3, and a set value 113 denotes a value for the data on the cross section B-B' in the case of X=3. In the example of FIG. 8A, it is desirable to set the value of X to be about 2 to 3. Of course, this value of X can be changed to a value that is separately input from a control screen. If the value of X is decreased, the detection of the high reflector can be made with a higher degree of sensitivity. If the value of X is increased, the detection of the high reflector can be made with a higher degree of uniqueness.

Figure 3A:
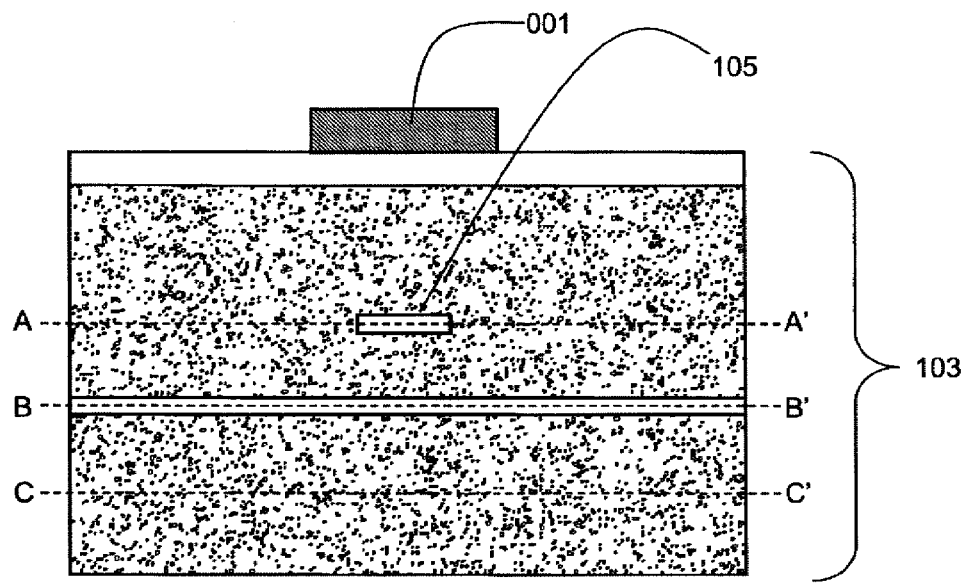
FIG. 3A is a view of a pseudo tissue model in which a lamellar structure exists.
Figure 3B:
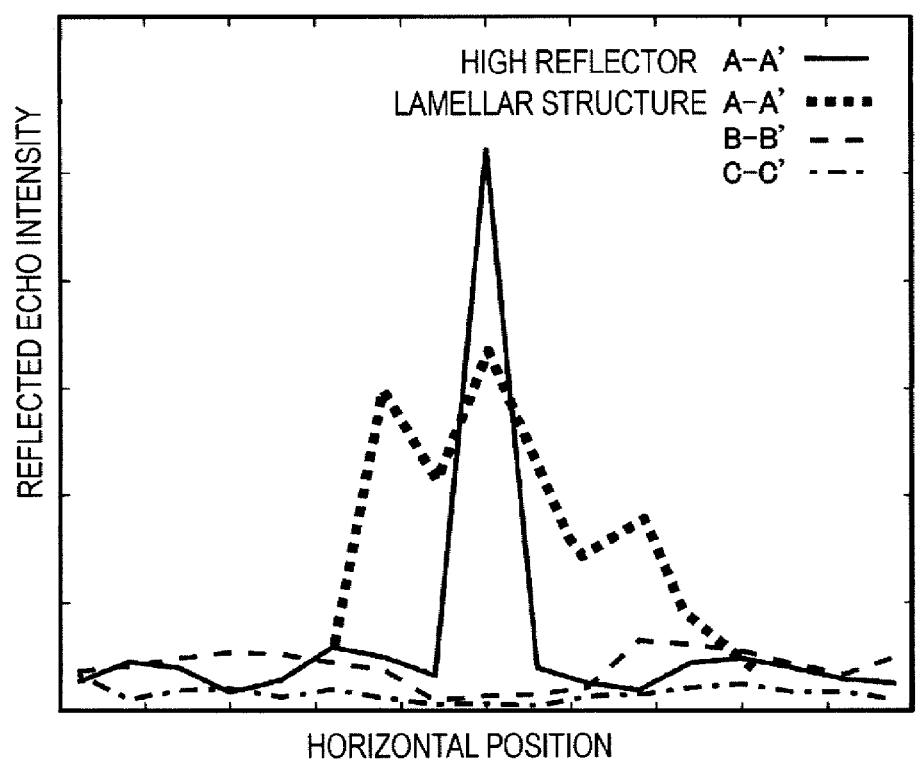
FIG. 3B is a view showing the intensities of reflected echoes therefrom.
Figure 8B:
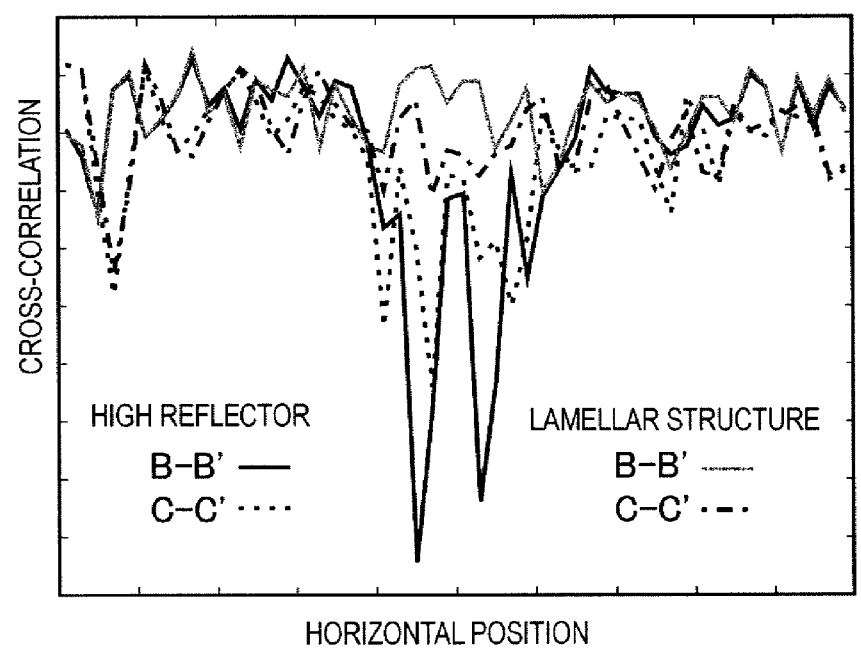

FIG. 8B is a graph in which the values of cross-correlations when similar processing is performed on a lamellar structure shown in FIG. 3A are plotted while being superimposed on the values of the cross-correlations of the high reflector shown in FIG. 8A. As can be seen from this graph, it is understood that in the case of the presence of the high reflector, the cross-correlation decreases, but in the case of the presence of the lamellar structure, the cross-correlation does not decrease. It can be understood that even if the intensities of the reflected echoes are of almost the same level (see FIG. 3B), there will be generated a clear difference in the cross-correlations in this manner. This means that even in case where the discrimination of a high reflector is difficult on an image in which the intensity of the reflected echo is displayed as a luminance value, it is possible to extract a candidate for a position in which the high reflector exists according to the technique of calculating cross-correlations in this embodiment.

As described above, in this embodiment, it is possible to extract an existence position candidate for a high reflector by calculating the cross-correlation of the received waveform data of adjacent scan lines in the depth direction, and by displaying a position at which the value of the cross-correlation thus calculated changes.

Second Embodiment

Hereafter, in a second embodiment, reference will be made to an example of a case in which not only the cross-correlation between adjacent scan lines but also the intensity thereof is used for detecting the position of a high reflector.

Figure 9:
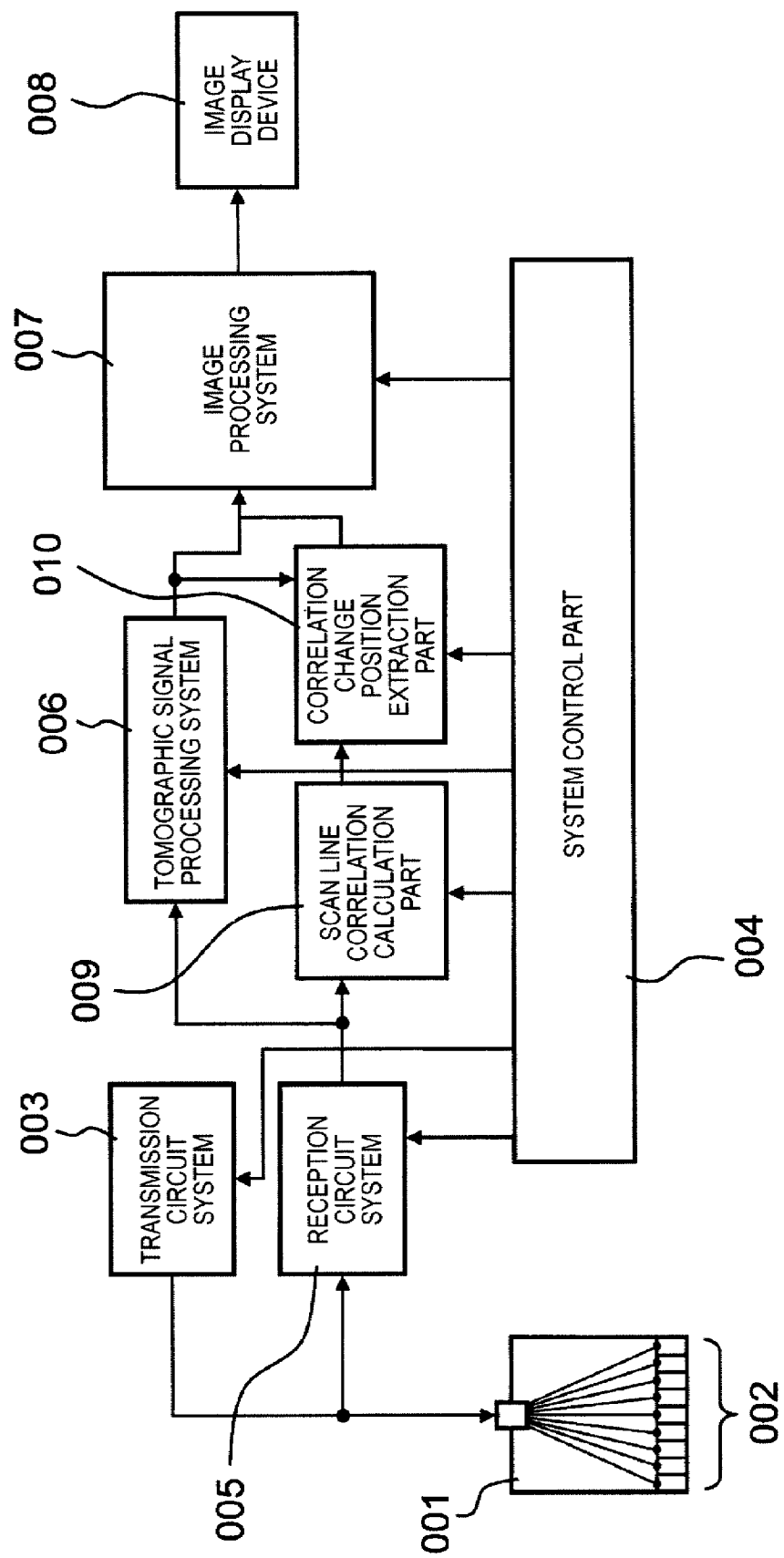
FIG. 9 is a block diagram of an ultrasonic apparatus according to a second embodiment of the present invention.

FIG. 9 is a system schematic diagram showing an ultrasonic apparatus according to this embodiment. The flow of signals displaying a tomographic image is the same as that of the first embodiment, and hence is omitted.

A reception circuit system 005 outputs received waveform data. A scan line correlation calculation part 009 calculates a cross-correlation between adjacent scan lines from the received waveform data input thereto. The scan line correlation calculation part 009 outputs the cross-correlation, and a correlation change position extraction part 010 extracts a position at which the correlation value changes as a first candidate for the existence position of a high reflector. Then, in order to acquire the intensity of an echo in a surrounding region of the first candidate, the correlation change position extraction part 010 receives, from a tomographic signal processing system 006, intensity data in the surrounding of the position at which the correlation value changes and the intensity data of a scan line that passes closest to or through the position at which the correlation value changes the position. The correlation change position extraction part 010 calculates, from the intensity data, an average value of intensities in the surrounding of the position at which the correlation value changes, and calculates the depth of a portion in which the intensity becomes higher than the above-mentioned average value in the surrounding of the position at which the correlation value changes. Then, the correlation change position extraction part 010 outputs depth information calculated from the intensity as the position information of the high reflector candidate, instead of depth information calculated from the correlation value. The image processing system 007 receives this position information, and superimposes the position information thus input on a tomographic image, and transmits it to an image display device 008, similar to the first embodiment.

With respect to the depth direction, the degree of change of the intensity is higher than that of the cross-correlation. Accordingly, in this embodiment, after the candidate position at which the high reflector exists is extracted according to the cross-correlation, the position in the depth direction thereof is narrowed by using the intensity data in the surrounding of the candidate position. By doing so, it is possible to extract the existence position candidate of the high reflector with still higher precision than in the first embodiment.

Third Embodiment

Hereafter, in a third embodiment, reference will be made to an ultrasonic apparatus that calculates a cross-correlation value from the received waveform data of adjacent scan lines, extracts an existence position candidate for a high reflector, and further estimates the physical property values of the high reflector from an intensity ratio of adjacent scan lines.

FIG. 10A is a system schematic diagram showing the ultrasonic apparatus according to this embodiment. FIG. 10B is a view showing the construction of a hatched region in FIG. 10A in detail. The processing of displaying a tomographic image is similar to that in the above-mentioned embodiments. A scan line correlation calculation part 021 outputs the cross-correlation of the received waveform data of adjacent scan lines. A correlation change position extraction part 023 detects a position at which the correlation value becomes equal to or less than a set value, and transmits the position information thus obtained to an image processing system 007 and a physical property calculation part 022.

The physical property calculation part 022 receives, from a tomographic signal processing system 006, the intensity data in the surrounding of the position (hereinafter referred to as a "first position") output from the correlation change position extraction part 023. Then, the physical property calculation part 022 calculates a first intensity ratio $\alpha$ that is an intensity ratio between the intensity of a scan line in a portion that is shallower than the first position and the intensity of an adjacent scan line at the same position as that of the first mentioned scan line. Subsequently, the physical property calculation part 022 calculates a second intensity ratio $\beta$ that is an intensity ratio between the intensity of the first mentioned scan line in a portion that is deeper than the first position and the intensity of the adjacent scan line at the same position as that of the first mentioned scan line. The reason for using the intensity ratios with the neighborhoods will be described below. An ultrasonic wave attenuates as it propagates, so there is a possibility that the calculated physical property values may be caused to vary under the influence of such attenuation when the intensity in the depth direction is compared as it is. The influence of the attenuation can be suppressed by taking a ratio of the intensity at a noted position with that in a vicinity thereof, in particular at the same depth.

A pseudo electric power transmission coefficient Tp, a pseudo electric power reflection coefficient Rp and a pseudo acoustic impedance Z are calculated according to the following equation 3 by the use of the values of these intensity ratios $\alpha$, $\beta$.

$$T_p = \left(\frac{\beta}{\alpha}\right)^{1/2}$$

$$R_p = 1 - \left(\frac{\beta}{\alpha}\right)^{1/2}$$

$$Z = \frac{Z_0 \left(\frac{\beta}{\alpha}\right)^{1/4}}{2 - \left(\frac{\beta}{\alpha}\right)^{1/4}}$$

(3)

Here, note that $Z_0$ can be substituted for by a general acoustic impedance of a living body, and a value of about from $1.35 \times 10^6$ to $1.7 \times 10^6$ kg/m$^2$·s is used.

The physical property calculation part 022 outputs these physical property values to the image processing system 007. The image processing system 007 uses a designated parameter among the pseudo electric power transmission coefficient Tp, the pseudo electric power reflection coefficient Rp, and the pseudo acoustic impedance Z. Then, the image processing system 007 generates an image signal in such a manner that these physical property parameters are displayed in a position extracted by the correlation change position extraction part 023 or outside a display area of a tomographic image, and displays the image signal on an image display device 008.

Further, a reference value, which is separately set, is provided in each of the three parameters of the pseudo electric power transmission coefficient Tp, the pseudo electric power reflection coefficient Rp, and the pseudo acoustic impedance Z, so that a display form is made to differ depending on the range of each parameter. Specifically, in accordance with the magnitude of the value of each parameter, the color or thickness of a marker indicating the position of a high reflector is changed, or the displayed color or typeface of a parameter being displayed is changed. By changing the display in this manner, the physical property values of the high reflector can be expressed. Thus, an operator can not only find the position candidate of the high reflector, but also intuitively understand the physical properties of an object to be examined, by seeing such a display, as a result of which the operator can perform the observation of the object to be examined, the detection of the high reflector and other operations in an efficient manner.

Here, reference will be made, as an example, to the change of the physical property values according to the kind of a calculus in a living body. In case where the composition of the calculus includes calcium apatite of 95% and calcium oxalate dihydrate of 5%, the acoustic impedance thereof is 4.2 kg/m$^2$·s. In the case of calcium oxalate monohydrate, the acoustic impedance is 9.2 kg/m$^2$·s. An energy reflectance R in an interface on which materials having different acoustic impedances Z1, Z2 are in contact with each other is represented as follows.

$$R = |(Z2-Z1)/(Z2+Z1)|^2$$

When assuming that an average acoustic impedance of the living body is about 1.5 kg/m$^2$·s, the energy transmittances T (=1−R) of the calculuses having the respective compositions are 77.6% and 48.2%, respectively. A reflected echo returning from a position deeper than the calculuses transmits through the interface of the calculuses four times, and can be calculated with T$^4$, resulting in energies of 36.3% and 54%, respectively. Thus, it is understood that the intensity of the reflected echo changes when the compositions of calculuses are different from each other, even in the case of the calculuses.

Fourth Embodiment

Figures 11A, 11B:
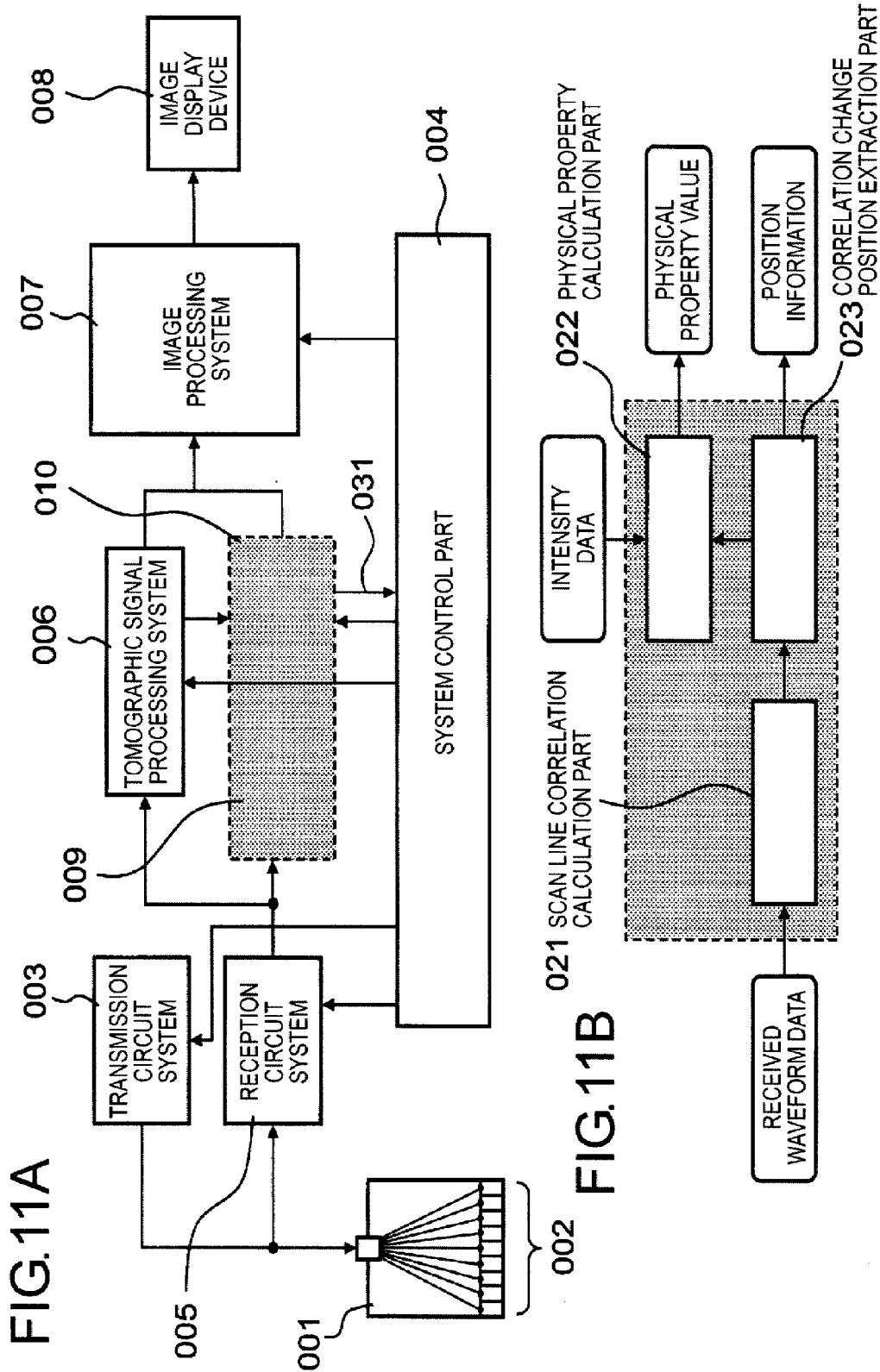
FIG. 11B and FIG. 11A are block diagrams of an ultrasonic apparatus according to a fourth embodiment of the present invention.

Hereinafter, in a fourth embodiment, reference will be made to an ultrasonic apparatus in which a transmission focus is changed according to a position candidate for a high reflector. FIG. 11A is a system concept view of the ultrasonic apparatus of this embodiment, and FIG. 11B is a view illustrating the construction of a hatched region of FIG. 11A in detail. The processing of displaying a tomographic image is similar to that in the above-mentioned embodiments, and hence is omitted. In this embodiment, the position information calculated by a correlation change position extraction part 023 is output to a system control part 004 (denoted by an arrow 031 in the figure). The system control part 004 with this position information being input thereto transmits a signal to a transmission circuit system 003 so that a scan line is formed with its transmission focus being set at that position. The received waveform data of the scan line thus set is input to a scan line correlation calculation part 021 again, and the physical properties thereof are calculated by a physical property calculation part 022.

Figure 12:
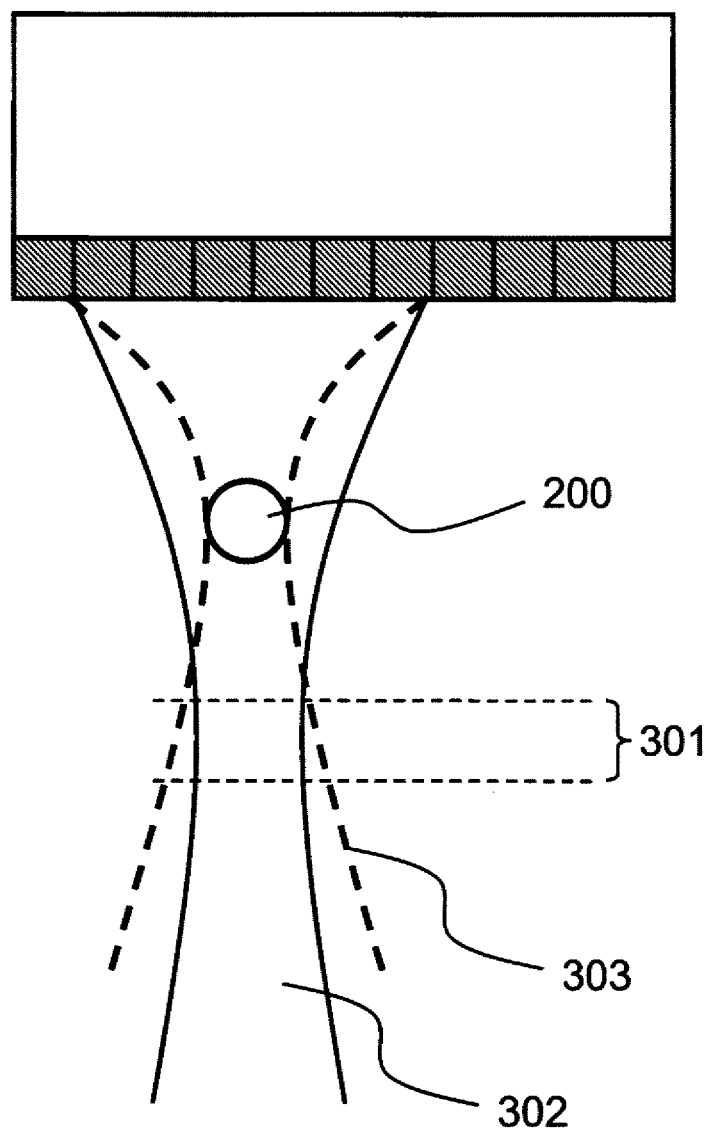
FIG. 12 is a view for explaining a transmission focus changing operation in the fourth embodiment.

The effect of this will be described by using FIG. 12. FIG. 12 is a view diagrammatically showing how a high reflector 200 exists in an object to be examined. A transmission beam 302 formed for displaying an ordinary tomographic image is set to have a transmission focus depth 301. In this case, some signals are transmitted and received while passing through sides of the high reflector 200, so signals are received which include, in a mixed manner, reflected waves that reflect the physical properties of the high reflector 200 and reflected waves that are transmitted and received while passing through the sides of the high reflector. However, when the position of the high reflector 200 is extracted and a transmission beam 303 is formed with its transmission focus being set to the position thus extracted, as in this embodiment, the proportion of the high reflector 200 that occupies the width of the transmission beam 303 increases as compared with the transmission beam 302. In other words, the proportion of the reflected waves that reflect the physical properties of the high reflector 200 in the received reflected waves increase. As a result, it becomes possible to calculate the existence position and physical properties of the high reflector 200 in a more accurate manner.

Here, note that if the transmission beam 303 with its transmission focus set to the position information is formed separately from the ordinary transmission and reception beams for displaying a tomographic image, it becomes possible to calculate the physical property values of the tomographic image without degrading the image quality thereof. In addition, if the transmission beam 303 is formed by correcting the position of the transmission focus of the transmission and reception beam for displaying the tomographic image, the calculation accuracy of the physical properties can be improved without dropping the frame rate.

Fifth Embodiment

In a fifth embodiment, reference will be made to an ultrasonic apparatus that is capable of extracting the position of a high reflector in the form of a unique region with further high precision.

First of all, note FIG. 8A. Though there exists a single high reflector, a decrease in the cross-correlation value is caused in two places across the high reflector. It is considered that the positions of the two places at which the cross-correlation value decreases denote positions corresponding to opposite ends of the high reflector because the cross-correlation value decreases when the ultrasonic beam is located at an end of the high reflector. In other words, the relation between the positions at which the cross-correlation value decreases and the position of the high reflector is associated with the relation between the size of the high reflector and the width of the ultrasonic beam. The ultrasonic apparatus of this embodiment extracts the position of the high reflector with further high precision by using such a phenomenon.

Figure 14:
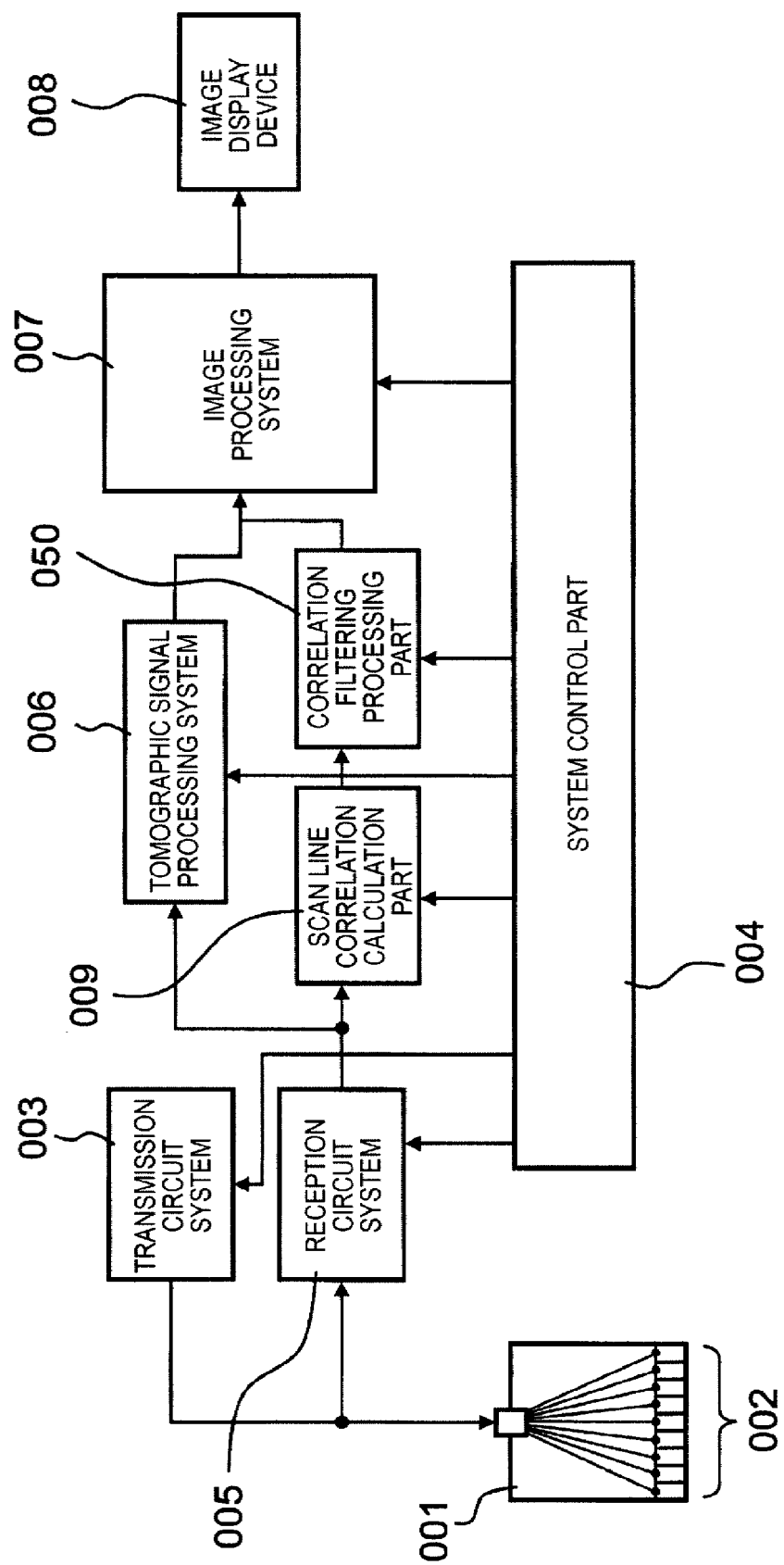
FIG. 14 is a block diagram of an ultrasonic apparatus according to a fifth embodiment of the present invention.

FIG. 14 is a view showing a system schematic diagram of the ultrasonic apparatus according to this embodiment. Description will be given to those portions which are different from the systems of the above-mentioned embodiments. The ultrasonic apparatus is provided with a correlation filtering processing part 050. A correlation value at each depth is output from a scan line correlation calculation block 009 to the correlation filtering processing part 050. The correlation filtering processing part 050 performs correlation filtering processing on the correlation values by using parameters input thereto from a system control part 004. When the result (a local minimum) of the correlation filtering processing is equal to or less than a threshold, the correlation filtering processing part 050 transmits the position information to an image processing system 007. The image processing system 007 displays the position information on an image display device 008 while superimposing it on a tomographic image. Here, note that the correlation filtering processing part 050 can use, as the above-mentioned threshold, a value which is obtained by subtracting X times a standard deviation from an average value of the results of the correlation filter processing. It is also possible for a user to change this value of X in a control screen as not shown in the figure. If the value of X is decreased, it will be possible to extract the high reflector with higher sensitivity, whereas if the value of X is increased, it will become possible to detect the high reflector with a higher degree of uniqueness.

Next, reference will be made to the correlation filtering processing by using FIG. 15. FIG. 15 depicts a model in which the correlation value decreases at opposite ends of the high reflector. In this embodiment, when considering that a function f (numeral 401) with drops at the position of the high reflector is observed while being transformed into a cross-correlation value distribution g (numeral 402), and denoting such a transformation matrix by H, the relation therebetween is expressed by the following equation.

$$g = Hf + n$$

where n is a noise vector.

An estimate $f_s$ for the function f is calculated from the cross-correlation value distribution g by using a Wiener filter.

$$f_s = Wg$$

$$W = FH^T(HFH^T + N)^{-1}$$

$$F = E[ff^T]$$

$$N = E[nn^T]$$

$$0 = E[fn^T]$$

where E[•] is an expectation value, and f and n are uncorrelated with each other.

$$\overline{f}_{ij} = \begin{cases} P_s/m & (i = j) \\ 0 & (i \neq j) \end{cases}$$

$$\overline{n}_{ij} = \begin{cases} P_n/m & (i = j) \\ 0 & (i \neq j) \end{cases}$$

$$h_{ij} = \begin{cases} 1 & (|i - j| = p) \\ 0 & (\text{else}) \end{cases}$$

However, Pn is calculated in a portion in which the cross-correlation value does not decrease, and satisfies the following relation: $Ps + Pn = g^T g$.

Figure 16:
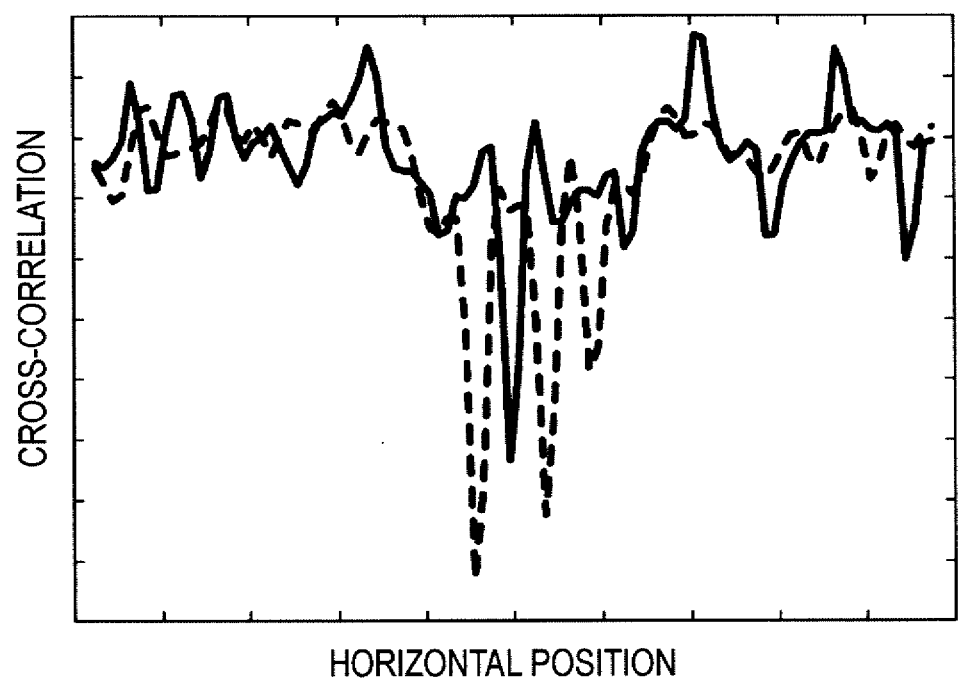
FIG. 16 is a view showing the result of processing in the fifth embodiment of the present invention.

FIG. 16 is the result of calculations thus performed. A graph denoted by a dotted line in this figure is the cross-correlation value between adjacent scan lines. A graph denoted by a solid line is the estimate of the function with the drops at the position of the high reflector that is calculated by using the above-mentioned Wiener filter. Thus, according to the ultrasonic apparatus of this embodiment, it is understood that even if decreases are seen at a plurality of positions in the cross-correlation value distribution, the position of the high reflector can be estimated with a higher degree of precision.

In addition, p in the equation is a value corresponding to the size of the high reflector. The system control part 004 gives a different value of p to the correlation filtering processing part, whereby a position candidate can be extracted for the high reflector that has a size corresponding to each value of p. In other words, the ultrasonic apparatus of this embodiment can estimate not only the position of the high reflector with higher precision, but also the size of the high reflector thus extracted. The ultrasonic apparatus with higher reliability can be provided by displaying the size of the high reflector thus estimated on an image together with the candidate position.

In case where a plurality of high reflectors exist adjacent to one another, the result of processing changes depending on the relation between the distances between the high reflectors and the width of the ultrasonic beam. In other words, the plurality of high reflectors are individually extracted, or the plurality of high reflectors are recognized as a single high reflector (i.e., they are extracted as a high reflector of a size represented by the external or outermost edge of the plurality of high reflectors). In either case, even when the plurality of high reflectors exist close to one another, the high reflectors can be extracted, and the intended effect of the present invention can be achieved.

Sixth Embodiment

In a sixth embodiment, reference will be made to an ultrasonic apparatus having a narrowed region in which correlation filtering processing is performed.

Figure 17:
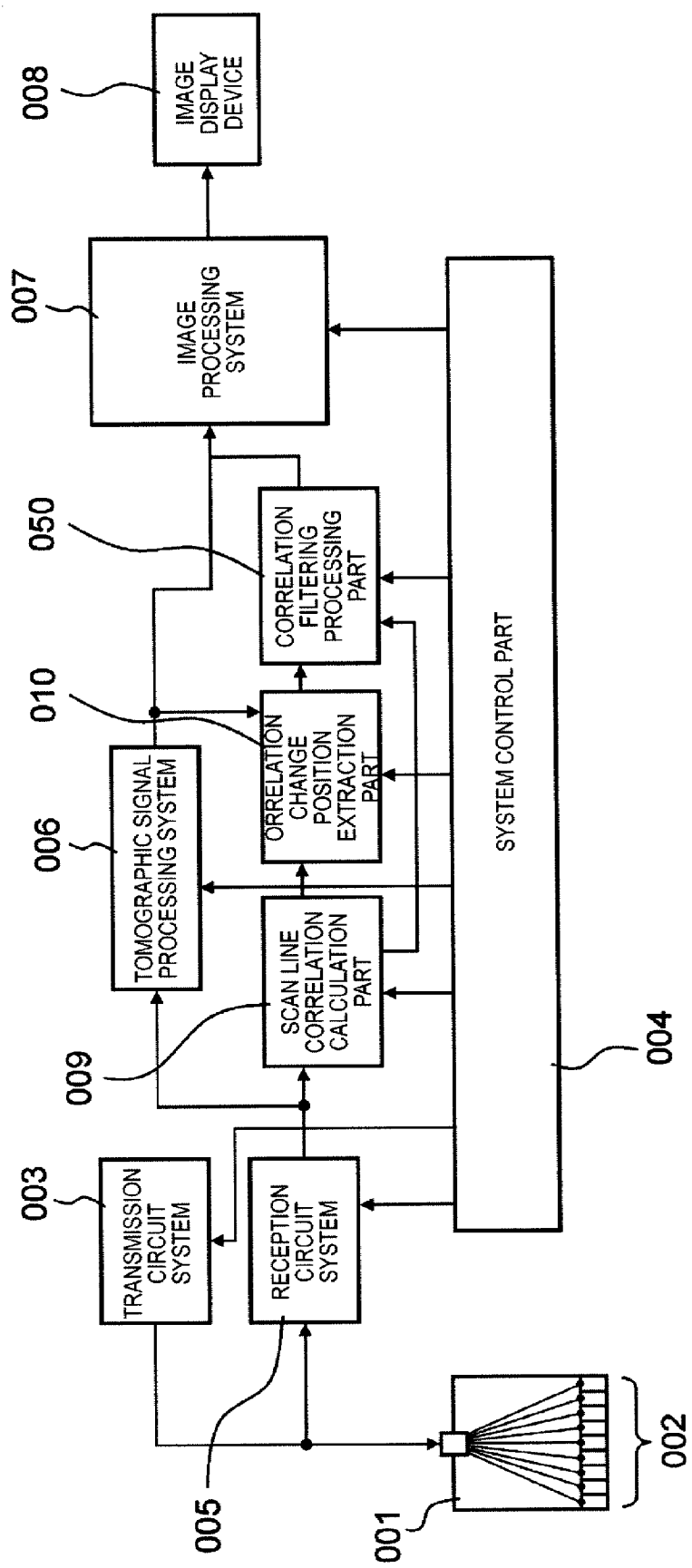
FIG. 17 is a block diagram of an ultrasonic apparatus according to a sixth embodiment of the present invention.

FIG. 17 is a system schematic diagram showing the ultrasonic apparatus according to this embodiment. Description will be given while focusing on those points which are different from the systems of the above-mentioned embodiments. A cross-correlation value calculated by a scan line correlation calculation block 009 is sent to a correlation change position extraction block 010 and a correlation filtering processing part 050. The correlation change position extraction block 010 extracts a portion in which the cross-correlation value becomes equal to or less than a predetermined value, and sends it to the correlation filtering processing part 050 as a position candidate. The correlation filtering processing part 050 outputs a position where a unique region can exist by performing correlation filtering processing with the use of the cross-correlation value (transmitted from the scan line correlation calculation block 009) in the surrounding of the position candidate sent from the correlation change position extraction block 010.

Figure 18:
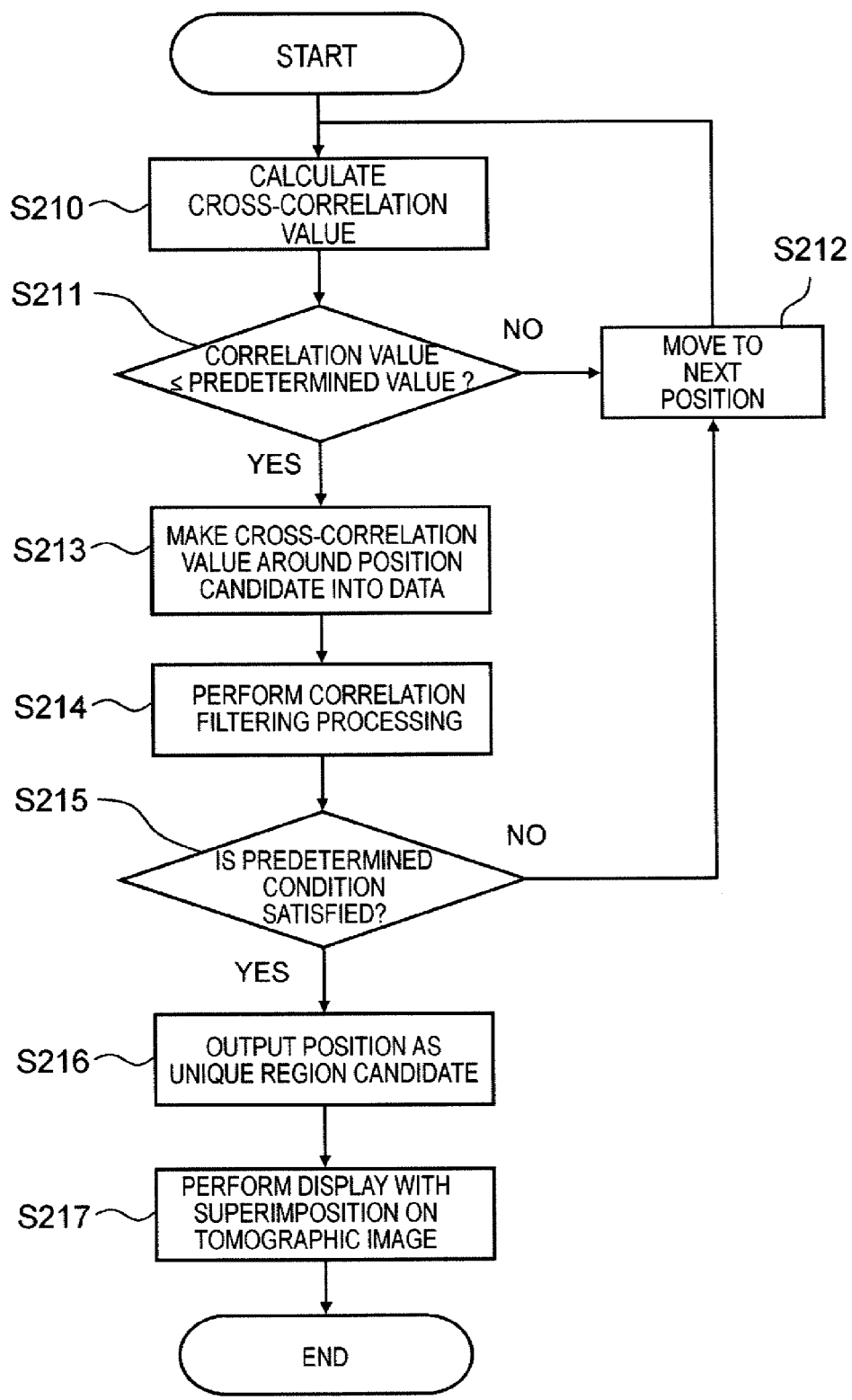
FIG. 18 is a flow chart explaining a positional procedure of the processing in the sixth embodiment of the present invention.

These steps will be further described by using FIG. 18. The scan line correlation calculation block 009 calculates a cross-correlation value for a certain noted depth (S210). The correlation change position extraction block 010 determines whether the cross-correlation value is equal to or lower than the predetermined value (S211). When the cross-correlation value is higher than the predetermined value, in other words, when there is no high reflector, the process is shifted to the following depth position or the following scan line (S212). When the cross-correlation value is equal to or lower than the predetermined value, the correlation change position extraction block 010 transmits a current position (scan line) and a noted depth to the correlation filtering processing part 050 as a position candidate. The correlation filtering processing part 050 sets a predetermined range (e.g., a region having a width of several tens of mm around the position candidate) based on this position candidate to a noted region, and makes the cross-correlation value obtained in this noted region into data (S213). Subsequently, the correlation filtering processing part 050 performs correlation filtering processing by using parameters transmitted thereto from a system control part 004 (S214). When the result of the correlation filtering processing satisfies a predetermined condition (e.g., a local minimum value is equal to or less than a threshold) (YES in S215), the correlation filtering processing part 050 makes a determination that a high reflector exists, and outputs position information thereof to the image processing system 007 as a candidate for the unique region (S216). In addition, filtering parameters or size information is input from the system control part 004 to the image processing system 007. The image processing system 007 displays the position information and the size information of the high reflector by superimposing them on a tomographic image (S217). At this time, the position information and the size information of the high reflector may be displayed with numerical values, or may be displayed by making the color or chroma thereof different from that of the tomographic image. Here, note that in step S214, the correlation filtering processing part 050 performs correlation filtering processing by using a plurality of filtering parameters corresponding to the different sizes of the high reflector. In case where a high reflector is not recognized even if the filtering parameters are changed within the range set by the system control part (NO in S215), the process is once ended, and the process is then shifted to the following depth position or the following scan line (S212).

By performing such processing, the correlation filtering processing is applied only to the limited data in the surrounding of the position candidate of the high reflector, so the processing scale can be decreased as compared with the case where correlation filtering processing is applied to the entire region. On the other hand, the position candidate is subjected to correlation filtering processing, so it becomes possible to perform the position extraction with higher accuracy as compared with the case where correlation filtering processing is not carried out.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-198500, filed on Jul. 31, 2008, which is hereby incorporated by reference herein in its entirety. This application claims the benefit of Japanese Patent Application No. 2009-51886, filed on Mar. 5, 2009, which is hereby incorporated by reference herein in its entirety.

The invention claimed is:

1. A signal processing apparatus which scans a beam of elastic waves into an object to be examined, acquires received waveform data of a plurality of scan lines, and performs signal processing to form a tomographic image of the object to be examined from the received waveform data of the plurality of scan lines, said apparatus comprising:
    a scan line correlation calculation part that calculates an individual cross-correlation between a first scan line and a second scan line, wherein the second scan line has a prescribed relation with the first scan line, for each of a plurality of positions on the scan lines; and
    a correlation change position extraction part that extracts, from among the plurality of positions on the scan lines, a position at which the correlation value calculated by said scan line correlation calculation part has a value different from a prescribed value, as a position at which a region of interest exists.

2. The signal processing apparatus as set forth in claim 1, wherein said correlation change position extraction part extracts, as the position at which the region of interest exists, a position at which the cross-correlation value has changed from a first value to a second value.

3. The signal processing apparatus as set forth in claim 1, wherein the prescribed relation between the first scan line and the second scan line is set such that the cross-correlation value of the first scan line and the second scan line is 0.5 or more.

4. The signal processing apparatus as set forth in claim 1, further comprising:
    an image processing part that displays the position at which the region of interest exists and which is output from said correlation change position extraction part while superimposing it on a tomographic image of the object to be examined.

5. The signal processing apparatus as set forth in claim 1, wherein said scan line correlation calculation part
    sets a noted position on the scan lines, extracts waveform data in a region of a predetermined width based on the noted position from the received waveform data of each of the first scan line and the second scan line, and obtains a cross-correlation value of the noted position by calculating a cross-correlation value between the extracted waveform data, and calculates individual cross-correlation values at a plurality of positions on the scan lines by moving the noted position.

6. The signal processing apparatus as set forth in claim 1, wherein said correlation change position extraction part extracts, as the position at which the region of interest exists, a position at which the cross-correlation has a value that is smaller than a prescribed set value by taking it as a position at which the correlation value becomes a value different from the prescribed value.

7. The signal processing apparatus as set forth in claim 1, wherein, after extracting a first candidate for the position at which the region of interest exists based on the correlation value, said correlation change position extraction part acquires echo intensities in a surrounding region of the first candidate, and outputs a position at which the echo intensity becomes higher than a predetermined value in the surrounding region, as the position at which the region of interest exists, in place of the first candidate.

8. The signal processing apparatus as set forth in claim 1, further comprising:

a physical property calculation part that, when a first position on the first scan line is extracted as the position at which the region of interest exists, calculates a physical property parameter in the first position by using a ratio of the echo intensities of the first scan line and the second scan line in a portion that is shallower than the first position, and a ratio of the echo intensities of the first scan line and the second scan line in a portion that is deeper than the first position.

9. A signal processing apparatus adapted to perform signal processing on signals obtained by receiving reflected signals of elastic waves from inside an object to be examined so as to form an image, said apparatus comprising:

a scan line correlation calculation part adapted to calculate and output, from received waveform data of at least two scan lines of the reflected signals, wherein the at least two scan lines have a prescribed relation to each other, a cross-correlation between the close scan lines; and a discrimination part adapted to extract position information in a depth direction inside the object to be examined from a change in the correlation value, and to discriminate the kind of a region of interest inside the object to be examined based on the correlation value after the change.

10. An ultrasonic apparatus adapted to scan a beam of ultrasonic waves, which are elastic waves, into an object to be examined, to acquire received waveform data of a plurality of scan lines, and to perform signal processing to form a tomographic image of the object to be examined from the received waveform data of the plurality of scan lines, said apparatus comprising:

a scan line correlation calculation part adapted to calculate an individual cross-correlation of received waveform data between a first scan line and a second scan line, wherein the second scan line that has a prescribed relation with the first scan line, for each of a plurality of positions on the scan lines; and a correlation change position extraction part adapted to extract, from among the plurality of positions on the scan lines, a position at which the correlation value becomes a value different from a prescribed value, as a position at which a region of interest containing a high reflector exists.

11. A control method for a signal processing apparatus adapted to acquire received waveform data of a plurality of scan lines reflected inside an object to be examined, and to perform signal processing to form a tomographic image of the object to be examined from the received waveform data of the plurality of scan lines, said method comprising:

a scan line correlation calculation step that calculates an individual cross-correlation of received waveform data between a first scan line and a second scan line, wherein the second scan line that has a prescribed relation with the first scan line, for each of a plurality of positions on the scan lines; and a correlation change position extraction step that extracts, from among the plurality of positions on the scan lines, a position at which the correlation value has a value different from a prescribed value, as a position at which a region of interest exists.

12. A control method for an ultrasonic apparatus adapted to acquire received waveform data of a plurality of scan lines reflected inside an object to be examined, and to form a tomographic image of the object to be examined from the received waveform data of the plurality of scan lines, said method comprising:

a scan line correlation calculation step of calculating an individual cross-correlation of received waveform data between a first scan line and a second scan line, wherein the second scan line that has a prescribed relation with the first scan line, for each of a plurality of positions on the scan lines; and a correlation change position extraction step of extracting, from among the plurality of positions on the scan lines, a position at which the correlation value has a value different from a prescribed value, as a position at which a region of interest containing a high reflector exists.

13. A signal processing apparatus adapted to scan a beam of elastic waves into an object to be examined, to acquire received waveform data of a plurality of scan lines, and to perform signal processing to form a tomographic image of the object to be examined from the received waveform data of the plurality of scan lines, said apparatus comprising:

a scan line correlation calculation part adapted to calculate an individual cross-correlation value of received waveform data between a first scan line and a second scan line, wherein the second scan line has a prescribed relation with the first scan line, for each of a plurality of positions on the scan lines; and a processing part adapted to apply, to a distribution in a scanning direction of a cross-correlation value calculated for a predetermined depth, transformation processing that transforms a first distribution shape with drops at opposite ends of a region of interest of a predetermined size into a second distribution shape with a drop in a central position of the region of interest, and estimates a position at which the region of interest exists by using the result of the transformation processing.

14. A signal processing apparatus adapted to scan a beam of elastic waves into an object to be examined, to acquire received waveform data of a plurality of scan lines, and to perform signal processing to form a tomographic image of the object to be examined from the received waveform data of the plurality of scan lines, said apparatus comprising:

a scan line correlation calculation part adapted to calculate an individual correlation value of received waveform data between a first scan line and a second scan line, wherein the second scan line has a prescribed relation with the first scan line, for each of a plurality of positions on the scan lines;

a correlation change position extraction part adapted to extract, from among the plurality of positions on the scan lines, a position at which the correlation value has a value different from a prescribed value as a position candidate for a position at which a region of interest exists; and a processing part adapted to apply, to a distribution in a scanning direction of a cross-correlation value calculated for a noted region set based on the position candidate, transformation processing that transforms a first distribution shape with drops at opposite ends of a region of interest of a predetermined size into a second distribution shape with a drop in a central position of the region of interest, and estimates a position at which the region of interest exists by using the result of the transformation processing.

15. A control method for a signal processing apparatus adapted to scan a beam of elastic waves into an object to be examined, to acquire received waveform data of a plurality of scan lines, and to perform signal processing to form a tomographic image of the object to be examined from the received waveform data of the plurality of scan lines, said method comprising:

a scan line correlation calculation step of calculating an individual cross-correlation value of received waveform data between a first scan line and a second scan line, wherein the second scan line has a prescribed relation with the first scan line, for each of a plurality of positions on the scan lines; and a transformation processing step of applying, to a distribution in a scanning direction of a cross-correlation value calculated for a predetermined depth, transformation processing that transforms a first distribution shape with drops at opposite ends of a unique region of interest of a predetermined size into a second distribution shape with a drop in a central position of the region of interest; and an estimation step of estimating a position at which the region of interest exists by using the result of the processing in said transformation processing step.

16. A signal processing apparatus adapted to scan a beam of elastic waves into an object to be examined, adapted to acquire received waveform data of a plurality of scan lines, and adapted to perform signal processing to form an image of the object to be examined from the received waveform data of the plurality of scan lines, said apparatus comprising:

a scan line correlation calculation part adapted to calculate an individual cross-correlation between a first scan line and a second scan line that has a prescribed relation with the first scan line, for a plurality of depth positions on the scan lines; and a correlation change position extraction part adapted to extract, from among the plurality of depth positions on the scan lines, a depth position at which the cross-correlation has a value that is smaller than a prescribed value or a depth position at which a rate of decrease of the cross-correlation value along the scan line is larger than a predetermined value, as a depth position at which a region of interest exists.

17. The signal processing apparatus as set forth in claim 16, wherein said correlation change position extraction part extracts, as the depth position at which the region of interest exists, a depth position at which the cross-correlation has a value that is smaller than the prescribed value, wherein the prescribed value is a value calculated from a plurality of the correlation values at the same depth position on the scan lines by subtracting a number of times a standard deviation of the plurality of correlation values from an average value of the plurality of correlation values at the same depth position.

18. The signal processing apparatus as set forth in claim 16, wherein the prescribed relation between the first scan line and said second scan line is set such that the cross-correlation value of the received waveform data between the first scan line and the second scan line is 0.5 or more.

19. The signal processing apparatus as set forth in claim 16, further comprising:

an image processing part adapted to cause an image display part to display the position at which the region of interest exists and which is output from said correlation change position extraction part while superimposing it on an image formed by using the received waveform data of the plurality of scan lines.

20. The signal processing apparatus as set forth in claim 16, wherein said scan line correlation calculation part is adapted to set a noted depth position on the scan lines, to extract waveform data in a region of a predetermined width based on the noted depth position from the received waveform data of each of the scan lines, and to obtain a cross-correlation value of the noted depth position by calculating a cross-correlation value between the extracted waveform data, and is adapted to calculate individual cross-correlation values at a plurality of depth positions on the scan lines by moving the noted depth position.

21. The signal processing apparatus as set forth in claim 16, wherein said correlation change position extraction part is adapted to acquire, after extracting a first candidate for the depth position at which the region of interest exists based on the correlation value, echo intensities in a surrounding region of the first candidate, and to output a depth position at which the echo intensity becomes higher than a predetermined value in the surrounding region, as the depth position at which the region of interest exists, in place of the first candidate.

22. The signal processing apparatus as set forth in claim 16, further comprising:

a physical property calculation part adapted to calculate, when a first depth position on the first scan line is extracted as the depth position at which the region of interest exists, a physical property parameter in the first depth position by using a ratio of the echo intensities of the first scan line and the second scan line in a portion that is shallower than the first depth position, and a ratio of the echo intensities of said first scan line and said second scan line in a portion that is deeper than the first depth position.

23. The signal processing apparatus as set forth in claim 16, wherein said apparatus is an ultrasonic apparatus, and said apparatus further comprising:

a probe adapted to transmit a beam of ultrasonic waves which are elastic waves into an object to be examined, and to receive reflected waves which are reflected inside the object to be examined; and a reception circuit system adapted to generate the received waveform data by using electric signals output from said probe.

24. A control method for a signal processing apparatus adapted to scan a beam of elastic waves into an object to be examined, to acquire received waveform data of a plurality of scan lines, and to perform signal processing to form an image of the object to be examined from the received waveform data of the plurality of scan lines, said method comprising:

a scan line correlation calculation step that calculates an individual cross-correlation between a first scan line and a second scan line that has a prescribed relation with the first scan line, for each of a plurality of depth positions on the scan lines; and a correlation change position extraction step that extracts, from among the plurality of depth positions on the scan lines, a depth position at which the cross-correlation has a value that is smaller than a prescribed value or a depth position at which a rate of decrease of the cross-correlation value along the scan line is larger than a predetermined value, as a depth position at which a region of interest exists.

25. The control method as set forth in claim 24, wherein, in said correlation change position extraction step, as the depth position at which the region of interest exists, a depth position at which the correlation value is smaller than the prescribed value is extracted, wherein the prescribed value is a value calculated from a plurality of the correlation values at the same depth position on the scan lines by subtracting a number of times a standard deviation of the plurality of correlation values from an average value of the plurality of correlation values at the same depth position.

26. The control method as set forth in claim 24, wherein the prescribed relation between the first scan line and the second scan line is set such that the cross-correlation value of the received waveform data between the first scan line and the second scan line is 0.5 or more.

27. The control method as set forth in claim 24, further comprising a display step, wherein the depth position at which the region of interest exists and which is output in said correlation change position extraction step is displayed by an image display part while being superimposed on an image formed by using the received waveform data of the plurality of scan lines.

28. The control method as set forth in claim 24, wherein, in said scan line correlation calculation step, a noted depth position is set on the scan lines, waveform data is extracted in a region of a predetermined width based on the noted depth position from the received waveform data of each of the scan lines, and a cross-correlation value of the noted depth position is obtained by calculating a cross-correlation value between the extracted waveform data, and individual cross-correlation values are calculated at a plurality of depth positions on the scan lines by moving the noted depth position.

29. The control method as set forth in claim 24, wherein, in said correlation change position extraction step, after a first candidate for the depth position at which the region of interest exists is extracted based on the cross-correlation value, echo intensities are acquired in a surrounding region of the first candidate, and a depth position at which the echo intensity becomes higher than a predetermined value in the surrounding region is output as the depth position at which the region of interest exists, in place of the first candidate.

30. The control method as set forth in claim 24, wherein, in said correlation change position extraction step, when a first depth position on the first scan line is extracted as the depth position at which the region of interest exists, a physical property parameter is calculated in the first depth position by using a ratio of the echo intensities of the first scan line and the second scan line in a depth portion that is shallower than the first depth position, and a ratio of the echo intensities of the first scan line and the second scan line in a portion that is deeper than the first depth position.

* * * * *